(12) United States Patent
Hamilton et al.

(10) Patent No.: US 7,098,211 B2
(45) Date of Patent: Aug. 29, 2006

(54) COMPOUNDS HAVING SIMULTANEOUS ABILITY TO BLOCK L-TYPE CALCIUM CHANNELS AND TO INHIBIT PHOSPHODIESTERASE TYPE 3 ACTIVITY

(75) Inventors: Gregory S. Hamilton, Catonsville, MD (US); Harry Jefferson Leighton, Boston, MA (US)

(73) Assignee: Artesian Therapeutics, Inc., Gaithersburg, MD (US)

( * ) Notice: Subject to any disclaimer, the term of this patent is extended or adjusted under 35 U.S.C. 154(b) by 207 days.

(21) Appl. No.: 10/679,303

(22) Filed: Oct. 7, 2003

(65) Prior Publication Data

US 2004/0242648 A1    Dec. 2, 2004

Related U.S. Application Data

(60) Provisional application No. 60/416,254, filed on Oct. 7, 2002.

(51) Int. Cl.
| | |
|---|---|
| C07D 401/04 | (2006.01) |
| C07D 401/12 | (2006.01) |
| C07D 401/14 | (2006.01) |
| A61K 31/501 | (2006.01) |

(52) U.S. Cl. .................. 514/252.03; 544/238
(58) Field of Classification Search ........... 544/238; 514/252.03
See application file for complete search history.

(56) References Cited

U.S. PATENT DOCUMENTS

| | | | |
|---|---|---|---|
| 4,450,165 | A | 5/1984 | Araki et al. |
| 4,564,619 | A | 1/1986 | Tanaka et al. |
| 4,568,677 | A | 2/1986 | Alker et al. |
| 4,590,195 | A | 5/1986 | Alker et al. |
| 4,723,014 | A | 2/1988 | Anderson et al. |
| 4,820,842 | A | 4/1989 | Anderson et al. |
| 4,876,255 | A | 10/1989 | Franckowiak et al. |
| 4,898,865 | A | 2/1990 | Franckowiak et al. |
| 5,096,904 | A | 3/1992 | Wheeler et al. |
| 5,100,892 | A | 3/1992 | Wheeler et al. |
| 5,258,519 | A | 11/1993 | Wheeler et al. |
| 5,344,944 | A | 9/1994 | Franckowiak et al. |

FOREIGN PATENT DOCUMENTS

| | | |
|---|---|---|
| DE | 101 10 747 A1 | 9/2002 |
| EP | 0 116 769 A1 | 8/1984 |
| EP | 0 119 050 A2 | 9/1984 |
| EP | 0 132 375 A2 | 1/1985 |
| EP | 0 185 964 A2 | 7/1986 |
| EP | 0 189 254 A1 | 7/1986 |
| EP | 0 268 273 A2 | 5/1988 |
| EP | 0 287 866 A1 | 10/1988 |
| EP | 0 287 867 A1 | 10/1988 |
| EP | 0 503 079 A1 | 9/1992 |
| EP | 1 302 463 A1 | 4/2003 |

OTHER PUBLICATIONS

Forest et al., "A Novel Class of Cardiotonic Agents: Synthesis and Biological Evaluation of 5-Substituted 3,6-Dihydrothiadiazin-2-ones with Cyclic AMP Phosphodiesterase Inhibiting and Myofibrillar Calcium Sensitizing Properties", *Journal of Medicinal Chemistry*, American Chemical Society, vol. 35, No. 1, 1992, pp. 163-172, XP002146828, ISSN: 0022-2623.

Rump et al., "Effects of Different Inotropes with Antioxidant Properties on acute Regional Myocardial Ischemia in Isolated Rabbit Hearts", *General Pharmacology*, Pergamon Press, Oxford, GB, vol. 26, No. 3, 1995, pp. 603-611, XP000926014, ISSN: 0306-3623.

Baraldi et al., "Synthesis and Calcium Antagonist Activity of Dialkyl 1,4-Dihydro-2,6-Dimethyl-4-(Nitrogenous Heteroaryl)-3,5-Pyridine Dicarboxylates", *Collect. Czech. Chem. Commun.*, vol. 57, 1992, pp. 169-178, XP009023953.

Alker et al., "Long Action Dihydropyridine Calcium Antagonists", *Journal of Medicinal Chemistry*, vol. 33, 1990, pp. 585-591, XP002267026.

Fossheim, "Crystal Structure of the Dihydropyridine $Ca^{2+}$ Antagonist Felodipine. Dihydropyridine Binding Prerequisites Assessed from Crystallographic Data," *J. Med. Chem.*, vol. 29, pp. 305-307, (1986), American Chemical Society.

Tamazawa et al., "Stereoselectivity of a Potent Calcium Antagonist, 1-Benzyl-3-pyrrolidinyl Methyl 2,6-Dimethyl-4-(m-nitrophenyl)-1,4-dihydropyridine-3,5-dicarboxylate," *J. Med. Chem.*, vol. 29, pp. 2504-2511, (1986) American Chemical Society.

Sunkel et al., "Synthesis of 3-[2,3-Dihydro-1,1,3-trioxo-1,2-benzisothiazol-2-yl]alkyl 1,4-Dihydropyridine-3,5-dicarboxylate Derivatives as Calcium Channel Modulators," *J. Med. Chem.*, vol. 35, pp. 2407-2414, (1992), American Chemical Society.

Arrowsmith et al., "Long-Acting Dihydropyridine Calcium Antagonists. 1. 2-Alkoxymethyl Derivatives Incorporating Basic Substituents," *J. Med. Chem.*, vol. 29, pp. 1696-1702, (1986), American Chemical Society, UK.

Alker, et al., "Long-Acting Dihydropyridine Calcium Antagonists. 5. Synthesis and Structure-Activity Relationships for a Series of 2-[[(N-Substituted-heterocyclyl)ethoxy]methyl]-1,4-dihydropyridine Calcium Antagonists," *J. Med. Chem.*, vol. 33, pp. 1805-1811, (1990), American Chemical Society, UK.

Rovnyak, et al., "Active Conformation of 1,4-Dihydropyridine Calcium Entry Blockers. Effect of Size of 2-Aryl Substituent on Rotameric Equilibria and Receptor Binding," *J. Med. Chem.*, vol. 34, pp. 2521-2524, (1991), American Chemical Society.

Goldmann, et al., "Synthesis, Pharmacological Effects, and Conformation of 4,4-Disubstituted 1,4-Dihydropyridines," *J. Med. Chem.*, vol. 33, pp. 1413-1418, (1990), American Chemical Society.

Atwal, et al., "Dihydropyrimidine Calcium Channel Blockers: 2-Heterosubstituted 4-Aryl-1,4-dihydro-6-methyl-5-pyrimidinecarboxylic Acid Esters as Potent Mimics of Dihydropyridines," *J. Med. Chem.*, vol. 33, pp. 1510-1515, (1990), American Chemical Society.

(Continued)

*Primary Examiner*—Kahsay Habte
(74) *Attorney, Agent, or Firm*—Seed IP Law Group PLLC

(57) ABSTRACT

The present invention provides compounds that possess inhibitory activity against PDE-3 and L-type calcium channels. The present invention further provides pharmaceutical compositions comprising such compounds and methods of using such compounds for treating cardiovascular disease, stroke, epilepsy, ophthalmic disorder or migraine.

14 Claims, 3 Drawing Sheets

OTHER PUBLICATIONS

Atwal, et al., "Dihydropyrimidine Calcium Channel Blockers. 2. 3-Substituted-4-aryl-1,4-dihydro-6-methyl-5-pyrimidinecarboxylic Acid Esters as Potent Mimics of Dihydropyridines," *J. Med. Chem.*, vol. 33, pp. 2629-2635, (1990), American Chemical Society.

Alker, et al., "Long-Acting Dihydropyridine Calcium Antagonists. 4. Synthesis and Structure-Activity Relationships for a Series of Basic and Nonbasic Derivatives of 2-[(2-Aminoethoxy)methyl]-1,4-dihydropyridine Calcium Antagonists," *J. Med. Chem.*, vol. 33, pp. 585-591, (1990), American Chemical Society.

Natale, et al., "Lipophilic 4-Isoxazolyl-1,4-dihydropyridines: Synthesis and Structure-Activity Relationships," *J. Med. Chem.*, vol. 42, pp. 3087-3093, (1999), American Chemical Society.

Malhotra et al., "Barnidipine," Drugs, vol. 61, pp. 989-996, (2001), Auckland, New Zealand.

Joslyn, et al., "Dimeric 1,4-Dihydropyridines as Calcium Channel Antagonists," *J. Med. Chem.*, vol. 31, pp. 1489-1492, (1988), American Chemical Society.

Alker, et al., "Long-Acting Dihydropyridine Calcium Antagonists. 3. Synthesis and Structure-Activity Relationships for a Series of 2-[(Heterocyclylmethoxy)methyl] Derivatives." *J. Med. Chem.*, vol. 32, pp. 2381-2388, (1989), American Chemical Society.

Novinson, et al., "3-Substituted 5,7-Dimethylpyrazolo[1,5-α]pyrimidines, 3',5'-Cyclic-AMP Phosphodiesterase Inhibitors," *J. Med. Chem.*, vol. 17, No. 6, pp. 645, 648, (1974).

Weishaar, et al., "A New Generation of Phosphodiesterase Inhibitors: Multiple Molecular Forms of Phosphodiesterase and the Potential for Drug Selectivity," *J. Med. Chem.*, vol. 28, No. 5, pp. 537-545, (1985), American Chemical Society, USA.

Coates, et al., "Cyclic Nucleotide Phosphodiesterase Inhibition by Imidazopyridines: Analogues of Sulmazole and Isomazole as Inhibitors of the cGMP Specific Phosphodiesterase," *J. Med. Chem.*, vol. 36, pp. 1387-1392, (1993), American Chemical Society.

Marivet, et al., "Inhibition of Cyclic Adenosine-3',5'-monophosphatae Phosphodiesterase from Vascular Smooth Muscle by Rolipram Analogues," *J. Med. Chem.*, vol. 32, pp. 1450-1457, (1989) American Chemical Society.

Moos, et al., "Cardiotonic Agents. 8. Selective Inhibitors of Adenosine 3',5'-Cyclic Phosphate Phosphodiesterase III. Elaboration of a Five-Point Model for Positive Inotropic Activity," *J. Med. Chem.*, vol. 30, pp. 1963-1972, (1987), American Chemical Society.

Venuti, et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," *J. Med. Chem.*, vol. 31, pp. 2136-2145, (1988), American Chemical Society.

Venuti, et al., "Inhibitors of Cyclic AMP Phosphodiesterase. 4. Synthesis and Evaluation of Potential Prodrugs of Lixazinone," *J. Med. Chem.*, vol. 31, pp. 2145-2152, (1988), American Chemical Society.

Sircar, et al., "Cardiotonic Agents, 7. Inhibition of Separated Forms of Cyclic Nucleotide Phosphodiesterase from Guinea Pig Cardiac Muscle by 4,5-Dihydro-6-[4-(1-H-imidazol-1-yl)phenyl]-3(2H)-pyridazinones and Related Compounds. Structure-Activity Relationships and Correlation with in Vivo Positive Inotropic Activity," *J. Med. Chem.*, vol. 30, pp. 1955-1962, (1987), American Chemical Society.

Sircar, et al., "Cardiotonic Agents. 9. Synthesis and Biological Evaluation of a Series of (E)-4,5-Dihydro-6-[2-[4-(1H-imidazol-1-yl)phenyl]ethenyl]-3(2H)-pyridazinones: A Novel Class of Compounds with Positive Inotropic, Antithrombotic, and Vasodilatory Activities for the Treatment of Congestive Heart Failure," *J. Med. Chem.*, vol. 32, pp. 342-250, (1989), American Chemical Society.

Garst, et al., "Inhibition of Separated Forms of Phosphodiesterases from Pig Coronary Arteries by Uracils and by 7-Substituted Derivatives of 1-Methyl-3-isobutylxanthine," *J. Med. Chem.*, vol. 19, No. 4, pp. 499-503, (1976).

Goodsell, et al., "8-Substituted Theophyllines. *In Vitro* Inhibition of 3'-5'-Cyclic Adenosine Monoposhate Phosphodiesterase and Pharmacological Spectrum in Mice," *Journal of Medicinal Chemistry*, vol. 14, No. 12 pp. 1202-1205, (1971).

Meanwell, et al., "Inhibitors of Blood Platelet cAMP Phosphodiesterase. 2. Structure-Activity Relationships Associated with 1,3-Dihydro-2H-imidazo[4,5-b]quinolin-2-ones Substituted with Functionalized Side Chains," *J. Med. Chem.*, vol. 35, pp. 2672-2687, (1992), American Chemical Society.

Wells, et al., "Inhibition of Separated Forms of Cyclic Nucleotide Phosphodiesterase from Pig Coronary Arteries by 1,3-Disubstituted and 1,3,8-Trisubstituted Xanthines," *J. Med. Chem.*, vol. 24, pp. 954-958, (1981), American Chemical Society.

Schneller, et al., "Inhibition of Cyclic Nucleotide Phosphodiesterases fro Pig Coronary Artery by Benzo-Separated Analogues of 3-Isobutyl-1-methylxanthine," *J. Med. Chem.*, vol. 29, pp. 972-978, (1986), American Chemical Society.

Buchman, et al., "Imidazole Derivatives as Inhibitors of Cyclic Nucleotide Phosphodiesterase," *J. Med. Chem.*, vol. 17, No. 11 pp. 1168-1173, (1974).

Lampe, et al., "(Imidazolylphenyl)pyrrol-2-one Inhibitor of Cardiac cAMP Phosphodiesterase," *J. Med. Chem.*, vol. 36, pp. 1041-1047, (1993), American Chemical Society.

Sircar, et al., "Cardiotonic Agents, 3. Synthesis and Biological Activity of Novel 6-(Substituted 1H-imidazol-4(5)-yl)-3(2H)-pyridazinones," *J. Med. Chem.*, vol. 29, pp. 261-267, (1986), American Chemical Society.

Novinson, et al., "2-(Alkylthio)-1,2,4-triazolo[1,5-a]pyrimidines as Adenosine Cyclic 3',5'-Monophosphate Phosphodiesterase Inhibitors with Potential as New Cardiovascular Agents," *J. Med. Chem.*, vol. 25, pp. 420-426, (1982) American Chemical Society.

Sircar, et al., "Cardiotonic Agents. 4. Synthesis and Biological Evaluation of N-Substituted 2,4,4a,5-Tetrahydro-3H-indeno[1,2-c]pyridazin-3-ones: Rigid Structures Derived from CI-930 and Analogues," *J. Med. Chem.*, vol. 29, pp. 2142-2148, (1986), American Chemical Society.

Sircar, et al., "Cardiotonic Agents. 2. Synthesis and Structure-Activity Relationships of 4,5-Dihydro-6-[4-(1H-imidazol-1-yl)phenyl]-3(2H)-pyridazinones: A New Class of Positive Inotropic Agents," *J. Med. Chem.*, vol. 28, pp. 1405-1413, (1985), American Chemical Society.

Harrison, et al., "Novel Alkaline Ring Cleavage of 2-Phenyl-3-hydroxythieno[2,3-b]quinoline 1,1-Dioxide, a Potent inhibitor of Cyclic Adenosine 5'-Monophosphate Phosphodiesterase," *J. Org. Chem.*, vol. 44, No. 17, pp. 2977-2979, (1979), American Chemical Society.

Meanwell, et al., "Inhibitors of Blood Platelet cAMP Phosphodiesterase. 3. 1,3-Dihydro-2H-imidazo[4,5-b]quinolin-2-one Derivatives with Enhanced Aqueous Solubility," *J. Med. Chem.*, vol. 35, pp. 2688-2696, (1992), American Chemical Society.

Sircar, et al., "Calcium Channel Blocking and Positive Inotropic Activities of Ethyl 5-Cyano-1,4-dihydro-6-methyl-2[(phenylsulfonyl)methyl]-4-aryl-3-pyridine-carboxylate and Analogues. Synthesis and Structure-Activity Relationships," *J. Med. Chem.*, vol. 34, pp. 2248-2260, (1991), American Chemical Society.

Coates, et al., "1,4-Bis(3-oxo-2,3-dihydropyridazin-6-yl)benzene Analogues: Potent Phosphodiesterase Inhibitors and Inodilators," *J. Med. Chem.*, vol. 33, pp. 1735-1741, (1990), American Chemical Society.

Sircar, et al., "1,2-Dihydro-5-[4-(1H-imidazol-1-yl)phenyl]-6-methyl-2-oxo-3-pyridinecarbonitriles and Related Compounds. Synthesis and Inotropic Activity," *J. Med. Chem.*, vol. 30, pp. 1023-1029, (1987).

Novinson, et al., "Adenosine Cyclic 3',5'-Monophosphate Phosphodiesterase Inhibitors, 2, 3-Substituted 5,7-Dialkylpyrazolo[1,5-a]pyrimidines," *Journal of Medicine Chemistry*, vol. 18, No. 5, pp. 460-464.

Sawanishi, et al., "Selective Inhibitors of Cyclic AMP-Specific Phosphodiesterase: Heterocycle-Condensed Purines," *J. Med. Chem.*, vol. 40, pp. 3248-3253, (1997), American Chemical Society.

Arrowsmith, et al., "Long Acting Dihydropyridine Calcium Antagonists. 2. 2-[2-Aminoheterocycloethoxy]methoxyl methyl Derivatives," *J. Med. Chem.*, vol. 32, pp. 562-568, (1989), American Chemical Society.

Nishi, et al., "Studies on 2-Oxoquinoline Derivatives as Blood Platelet Aggregation Inhibitors. III. N-Cyclohexyl-N(2- hydroxyethyl)-4-(1,2-dihydro-2-oxo-6-quinolyloxy)-butyramide and Related Compounds," *Chem. Pharm. Bull.*, vol. 31, No. 3 pp. 852-860, (1983).

Lugnier, et al., "Substituted carbostyrils as inhibitors of cyclic AMP phosphodiesterase," *Eur. J. Med. Chem.—Chim. Ther.*, vol. 20, No. 2 pp. 121-125, (1985).

Jones, et al., "Inhibitors of Cyclic AMP Phosphodiesterase. 1. Analogues of Cilostamide and Anagrelide," *J. Med. Chem.*, vol. 30, pp. 295-303, (1987), American Chemical Society.

Results of computer search in *Chemical Abstracts Registry*, comprising Parts I to IV.

COMPOUNDS HAVING SIMULTANEOUS ABILITY TO BLOCK L-TYPE CALCIUM CHANNELS AND TO INHIBIT PHOSPHODIESTERASE TYPE 3 ACTIVITY

This application claims the benefit of U.S. Provisional Patent Application No. 60/416,254, filed Oct. 7, 2002, the entire contents of which are herein incorporated by reference.

Congestive heart failure affects an estimated 4.8 million Americans with over 400,000 new cases diagnosed each year. Despite incremental advances in drug therapy, the prognosis for patients with advanced heart failure remains poor with annual mortality exceeding 40 percent. Although heart transplantation is an effective therapy for patients with advanced heart failure, less than 2,200 heart transplants are performed annually due to a limited supply of donor organs. Recent analyses indicate that further increases in the incidence and prevalence of advanced heart failure are likely, highlighting the pressing need for novel and effective therapeutic strategies.

During heart failure, there is an alteration of calcium homeostasis, including impaired sarcoplasmic reticulum calcium re-uptake, increased basal (diastolic) calcium levels, decreased peak (systolic) calcium and reduced rate of calcium transients, resulting in a decreased force of contraction and a slowing of relaxation. The end results of these abnormalities in calcium homeostasis are depressed contractile function (decreased contractility and cardiac output), impaired ventricular relaxation, and myocyte loss via ischemia and/or apoptosis-related mechanisms. Disregulation of calcium homeostasis has also been implicated in a number of other disease states, including stroke, epilepsy, ophthalmic disorders and migraine.

Selective inhibitors of the type 3 phosphodiesterase (PDE-3) found in cardiac muscle, such as amrinone and milrinone, have been evaluated for the treatment of congestive heart failure. Such compounds produce positive inotropic effects (increased contractility of heart muscle) by enhancing cAMP levels, which results in the activation of protein kinase A (PKA). Phosphorylation of the PKA substrate protein phospholamban causes an increased uptake of intracellular calcium into the sarcoplasmic reticulum (SR), thereby affecting cardiac contractility, as well as increasing ventricular relaxation (lusitrophism). However, at high doses, PDE inhibitors may increase heart rate and cardiac output, and cause arrhythmia. These adverse effects of PDE inhibitors thus limit their utility in the treatment of heart failure. The failure of PDE inhibition alone to normalize calcium signaling is due to another effect of enhanced cAMP levels in cardiomyocytes: PKA activates voltage-dependent L-type calcium channels in the myocyte membrane, allowing extracellular calcium to enter the cell.

Selective inhibitors of L-type calcium channels, such as the clinically used agent nifedipine, decrease the influx of extracellular calcium into cardiomyocytes by blocking the voltage-dependent calcium channels, thereby decreasing heart rate and exerting anti-ischemic effects.

The above suggests that a pharmacological agent which is capable of simultaneously inhibiting phosphodiesterase activity, resulting in increased ventricular relaxation and contractility, while preventing increased influx of extracellular calcium through voltage-dependent calcium channels, will have the desired effect of normalizing calcium homeostasis in failing heart, thereby producing therapeutic benefits without the adverse effects of PDE inhibition alone. Thus, there is a critical need for agents that are potent inhibitors of both PDE-3 and L-type calcium channels.

SUMMARY OF THE INVENTION

This invention provides compounds that possess inhibitory activity against PDE-3 and L-type calcium channels. This invention further provides pharmaceutical compositions comprising such compounds and methods of using such compounds for treating cardiovascular disease, stroke, epilepsy, ophthalmic disorder or migraine.

DETAILED DESCRIPTION

Definitions

Figure 1:
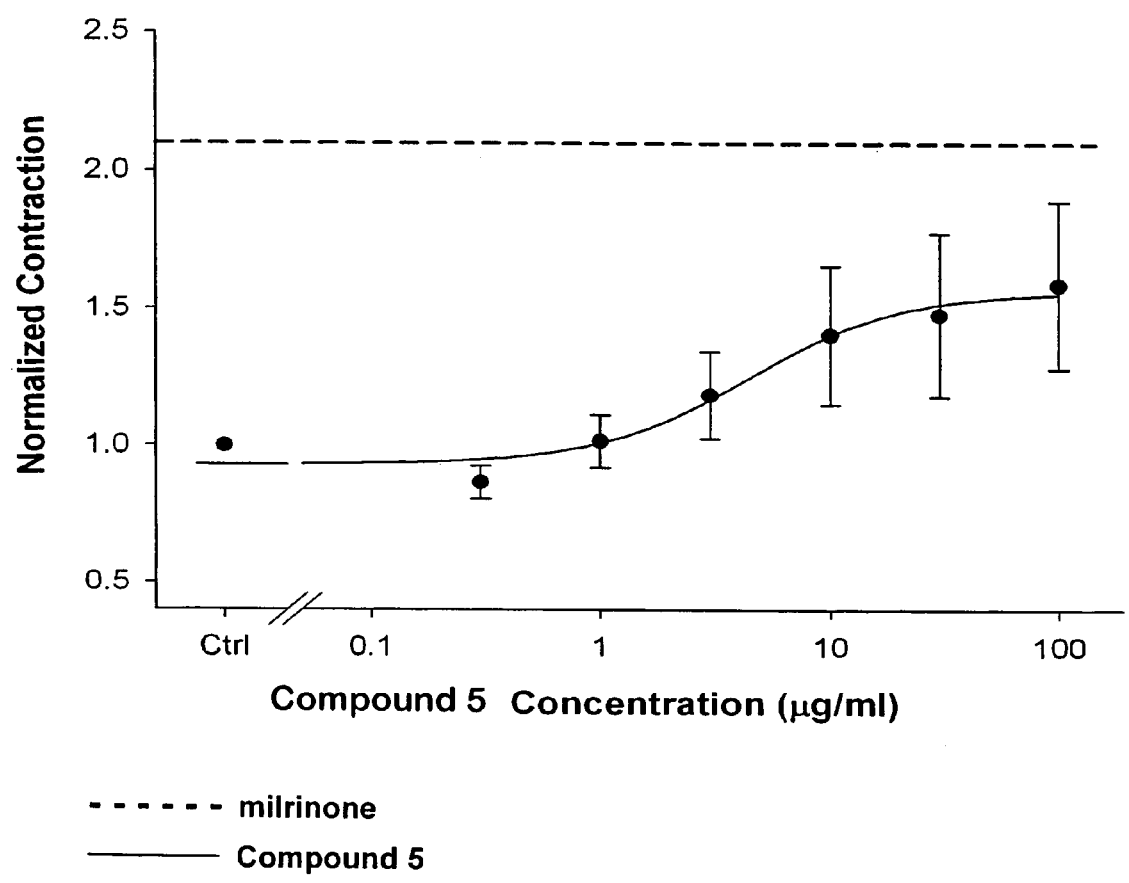
FIG. 1 is a graph showing normalization of myocardial contractility by Compound 5 in guinea-pig papillary muscle.

"Alkyl" refers to a saturated straight or branched chain hydrocarbon radical. Examples include without limitation methyl, ethyl, propyl, iso-propyl, butyl, iso-butyl, tert-butyl, n-pentyl and n-hexyl.

"Alkylene" refers to a divalent alkyl radical.

"Alkylthio" refers to a sulfur substituted alkyl radical.

"Alkenyl" refers to an unsaturated straight or branched chain hydrocarbon radical comprising at least one carbon to carbon double bond. Examples include without limitation ethenyl, propenyl, iso-propenyl, butenyl, iso-butenyl, tert-butenyl, n-pentenyl and n-hexenyl.

"Alkenylene" refers to a divalent alkenyl radical.

"Alkynyl" refers to an unsaturated straight or branched chain hydrocarbon radical comprising at least one carbon to carbon triple bond. Examples include without limitation ethynyl, propynyl, iso-propynyl, butynyl, iso-butynyl, tert-butynyl, pentynyl and hexynyl.

"Alkynylene" refers to a divalent alkynyl radical.

"Cycloalkyl" refers to a cyclic alkyl radical. Examples include without limitation cyclobutyl, cycopentyl, cyclohexyl, cycloheptyl and cyclooctyl.

"Cycloalkenyl" refers to a cyclic alkenyl radical. Examples include without limitation cyclopentenyl, cyclohexenyl, cycloheptenyl and cyclooctenyl.

"Alkoxy" refers to an alkyl group bonded through an oxygen linkage.

"Alkenoxy" refers to an alkenyl group bonded through an oxygen linkage.

"Substituted phenyl" refers to a phenyl that is substituted with one or more substituent(s). Examples of such substituents include without limitation $C_1$–$C_6$ alkyl, $C_2$–$C_6$ alkenyl, $C_2$–$C_6$ alkynyl, $C_1$–$C_6$ alkoxy, $C_2$–$C_6$ alkenyloxy, phenoxy, benzyloxy, hydroxy, carboxy, hydroperoxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, nitro, nitroso, isonitroso, nitrosamino, imino, nitrosimino, oxo, $C_1$–$C_6$ alkylthio, sulfamino, sulfamoyl, sulfeno, sulfhydryl, sulfinyl, sulfo, sulfonyl, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, disilanyl, siloxy, silyl, silylene and carbocyclic and heterocyclic moieties.

"Aryl" refers to a cyclic aromatic hydrocarbon moiety having one or more closed ring(s). Examples include without limitation phenyl, benzyl, naphthyl, anthracenyl, phenanthracenyl and biphenyl.

"Heteroaryl" refers to a cyclic aromatic moiety having one or more closed rings with one or more heteroatom(s) (for example, sulfur, nitrogen or oxygen) in at least one ring. Examples include without limitation pyrryl, furanyl, thienyl, pyridinyl, oxazolyl, thiazolyl, benzofuranyl, benzothienyl, benzofuranyl and benzothienyl.

"Halo" refers to a fluoro, chloro, bromo or iodo radical.

"Isosteres" refer to elements, functional groups, substituents, molecules or ions having different molecular formulae but exhibiting similar or identical physical properties. For example, tetrazole is an isostere of carboxylic acid because it mimics the properties of carboxylic acid even though they have different molecular formulae. Typically, two isosteric molecules have similar or identical volumes and shapes. Ideally, isosteric molecules should be isomorphic and able to co-crystallize. Other physical properties that isosteric molecules usually share include boiling point, density, viscosity and thermal conductivity. However, certain properties may be different: dipolar moments, polarity, polarization, size and shape since the external orbitals may be hybridized differently. The term "isosteres" encompasses "bioisosteres."

"Bioisosteres" are isosteres that, in addition to their physical similarities, share some common biological properties. Typically, bioisosteres interact with the same recognition site or produce broadly similar biological effects.

"Effective amount" refers to the amount required to produce a desired effect, for example: regulating calcium homeostasis; treating a disease, condition in which disregulation of calcium homeostasis is implicated; treating a cardiovascular disease, stroke, epilepsy, ophthalmic disorder or migraine; or inhibiting PDE (for example, PDE-3) or L-type calcium channels.

"Metabolite" refers to a substance produced by metabolism or by a metabolic process.

"Pharmaceutically acceptable carrier" refers to a pharmaceutically acceptable material, composition or vehicle, such as a liquid or solid filler, diluent, excipient or solvent encapsulating material, involved in carrying or transporting the subject compound from one organ, or portion of the body, to another organ or portion of the body. Each carrier is "acceptable" in the sense of being compatible with the other ingredients of the formulation and suitable for use with the patient. Examples of materials that can serve as a pharmaceutically acceptable carrier include without limitation: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically acceptable equivalent" includes, without limitation, pharmaceutically acceptable salts, hydrates, solvates, metabolites, prodrugs and isosteres. Many pharmaceutically acceptable equivalents are expected to have the same or similar in vitro or in vivo activity as the compounds of the invention.

"Pharmaceutically acceptable salt" refers to an acid or base salt of the inventive compounds, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Prodrug" refers to a derivative of the inventive compounds that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using conventional methods, such as that described in BURGER'S MEDICINAL CHEMISTRY AND DRUG CHEMISTRY, Fifth Ed., Vol. 1, pp. 172–178, 949–982 (1995).

"Isomers" refer to compounds having the same number and kind of atoms, and hence the same molecular weight, but differing with respect to the arrangement or configuration of the atoms.

"Stereoisomers" refer to isomers that differ only in the arrangement of the atoms in space.

"Diastereoisomers" refer to stereoisomers that are not mirror images of each other. Diastereoisomers occur in compounds having two or more asymmetric carbon atoms; thus, such compounds have $2^n$ optical isomers, where n is the number of asymmetric carbon atoms.

"Enantiomers" refers to stereoisomers that are non-superimposable mirror images of one another.

"Enantiomer-enriched" refers to a mixture in which one enantiomer predominates.

"Racemic" refers to a mixture containing equal parts of individual enantiomers.

"Non-racemic" refers to a mixture containing unequal parts of individual enantiomers.

"Animal" refers to a living organism having sensation and the power of voluntary movement, and which requires for its existence oxygen and organic food. Examples include, without limitation, members of the human, equine, porcine, bovine, murine, canine and feline species. In the case of a human, an "animal" may also be referred to as a "patient."

"Mammal" refers to a warm-blooded vertebrate animal.

"Calcium homeostasis" refers to the internal equilibrium of calcium in a cell.

"Cardiovascular disease" refers to a disease of the heart, blood vessels or circulation.

"Heart failure" refers to the pathophysiologic state in which an abnormality of cardiac function is responsible for the failure of the heart to pump blood at a rate commensurate with the requirements of the metabolizing tissues.

"Congestive heart failure" refers to heart failure that results in the development of congestion and edema in the metabolizing tissues.

"Hypertension" refers to elevation of systemic blood pressure.

"SA/AV node disturbance" refers to an abnormal or irregular conduction and/or rhythm associated with the sinoatrial (SA) node and/or the atrioventricular (AV) node.

"Arrhythmia" refers to abnormal heart rhythm. In arrhythmia, the heartbeats may be too slow, too fast, too irregular or too early. Examples of arrhythmia include, without limitation, bradycardia, fibrillation (atrial or ventricular) and premature contraction.

"Hypertrophic subaortic stenosis" refers to enlargement of the heart muscle due to pressure overload in the left ventricle resulting from partial blockage of the aorta.

"Angina" refers to chest pain associated with partial or complete occlusion of one or more coronary arteries in the heart.

"Treating" refers to: (i) preventing a disease, disorder or condition from occurring in an animal that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

Compounds

The present invention provides compounds possessing inhibitory activity against PDE-3 and L-type calcium channels, of the general formula

Y-L-X wherein:
  Y is a dihydropyridine L-type calcium channel blocker moiety;
  L is a linking group; and
  X is a PDE-3 inhibitory moiety.
Examples of dihydropyridine L-type calcium channel blockers include without limitation:

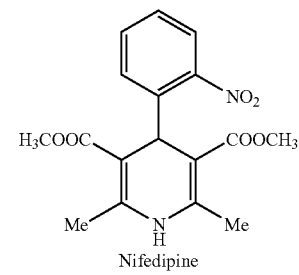
Nifedipine

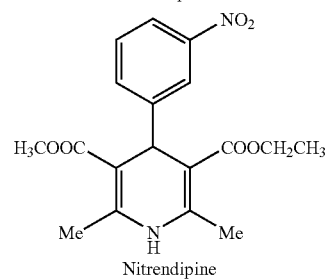
Nitrendipine

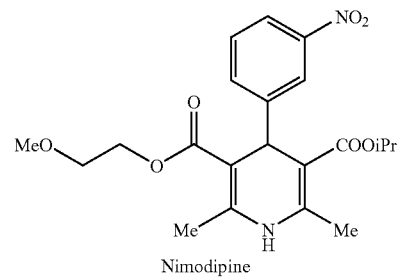
Nimodipine

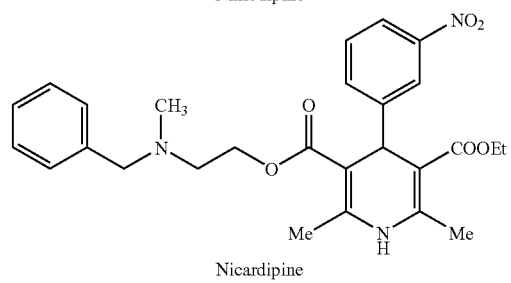
Nicardipine

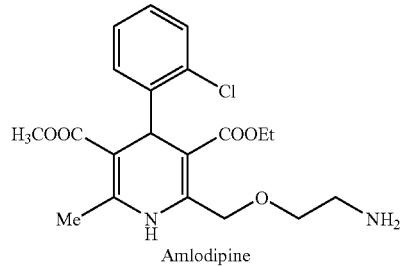
Amlodipine

One embodiment of the present invention encompasses a compound of formula I

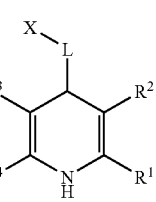

or a pharmaceutically acceptable equivalent, an isomer or a mixture of isomers thereof, wherein:

$R^1$ and $R^4$ are independently hydrogen, halo, nitro, cyano, trifluoromethyl, amino, —$NR^5R^6$, $C_1$–$C_4$ alkoxy, $C_1$–$C_4$ alkylthio, $C_1$–$C_8$ alkyl, $C_2$–$C_8$ alkenyl or $C_2$–$C_8$ alkynyl, wherein one or more —$CH_2$— group(s) of the alkyl, alkenyl or alkynyl is/are optionally replaced with —O—, —S—, —$SO_2$— and/or —$NR^5$—, and the alkyl, alkenyl or alkynyl is optionally substituted with one or more carbonyl oxygen(s) and/or hydroxyl(s);

$R^5$ and $R^6$ are independently hydrogen, $C_1$–$C_8$ alkyl, $C_2$–$C_8$ alkenyl or $C_2$–$C_8$ alkynyl, wherein the alkyl, alkenyl or alkynyl is optionally substituted with phenyl or substituted phenyl;

$R^2$ and $R^3$ are independently —$COOR^7$, nitro, cyano or trifluoromethyl;

$R^7$ is $C_1$–$C_8$ alkyl, $C_2$–$C_8$ alkenyl or $C_2$–$C_8$ alkynyl, wherein the alkyl, alkenyl or alkynyl is optionally substituted with $C_1$–$C_4$ alkoxy or —$NR^5R^6$;

L is a direct bond, $C_1$–$C_{12}$ alkylene, $C_2$–$C_{12}$ alkenylene or $C_2$–$C_{12}$ alkynylene, wherein one or more —$CH_2$— group(s) of the alkylene, alkenylene or alkynylene is/are optionally replaced with —O—, —S—, —$SO_2$— and/or —$NR^5$—, and the alkylene, alkenylene or alkynylene is optionally substituted with one or more carbonyl oxygen(s) and/or hydroxyl(s); and X is a moiety of formula A, B, C, D, E, F, G, H, I, J, K, L, M, N, O, P or Q

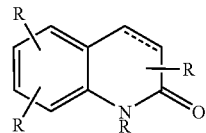

A

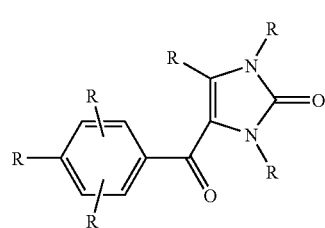

B

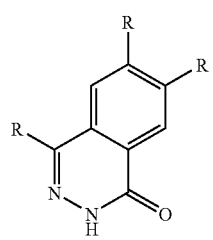

C

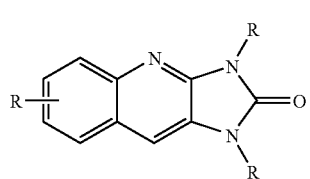

D

-continued

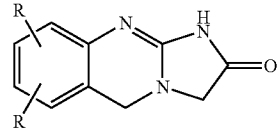

E

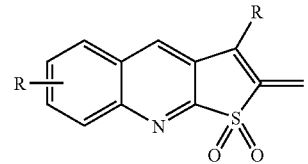

F

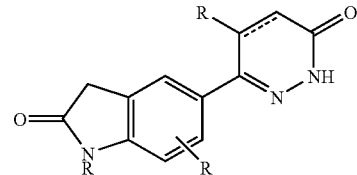

G

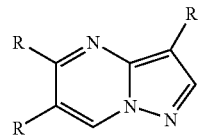

H

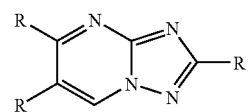

I

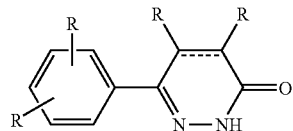

J

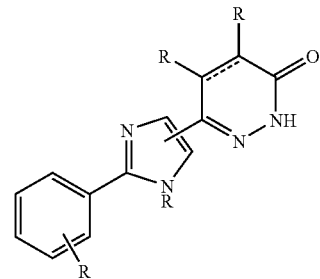

K

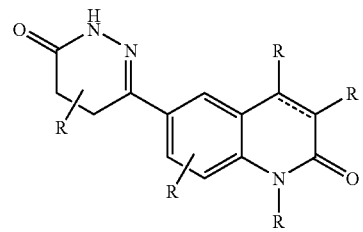

L

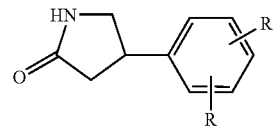

M

-continued

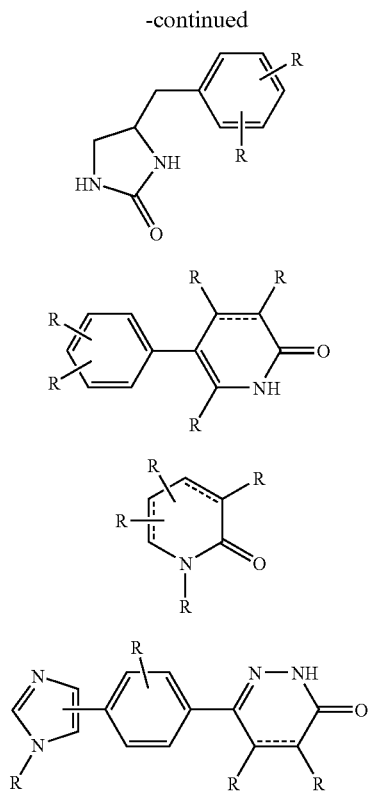

with X connected to L through any one R; and each R is independently a direct bond, hydrogen, halo, nitro, cyano, trifluoromethyl, amino, —NR$^5$R$^6$, $C_1$–$C_4$ alkoxy, $C_1$–$C_4$ alkylthio, —COOR$^7$, $C_1$–$C_{12}$ alkyl $C_2$–$C_{12}$ alkenyl or $C_2$–$C_{12}$ alkynyl, wherein one or more —CH$_2$— group(s) of the alkyl, alkenyl or alkynyl is/are optionally replaced with —O—, —S—, —SO$_2$— and/or —NR$^5$—, and the alkyl, alkenyl or alkynyl is optionally substituted with one or more carbonyl oxygen(s) and/or hydroxyl(s).

In one embodiment of formula I, when X is a moiety of formula A and L is a direct bond, then L is connected to the phenyl ring of A.

In another embodiment of formula, I, R$^1$ and R$^4$ are each $C_1$–$C_4$ alkyl, R$^2$ and R$^3$ are each —COOR$^7$, L is a direct bond, and X is a moiety of formula A or P.

Examples of compounds of formula I include without limitation:

(Compound 1)

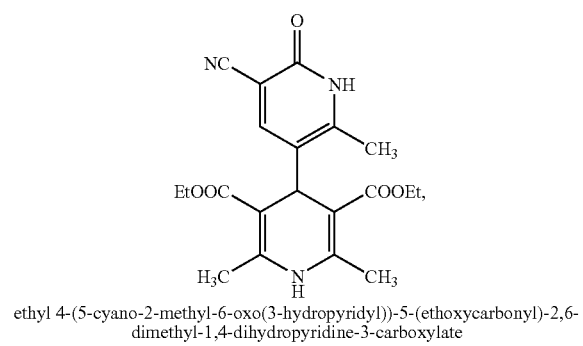

ethyl 4-(5-cyano-2-methyl-6-oxo(3-hydropyridyl))-5-(ethoxycarbonyl)-2,6-dimethyl-1,4-dihydropyridine-3-carboxylate -continued

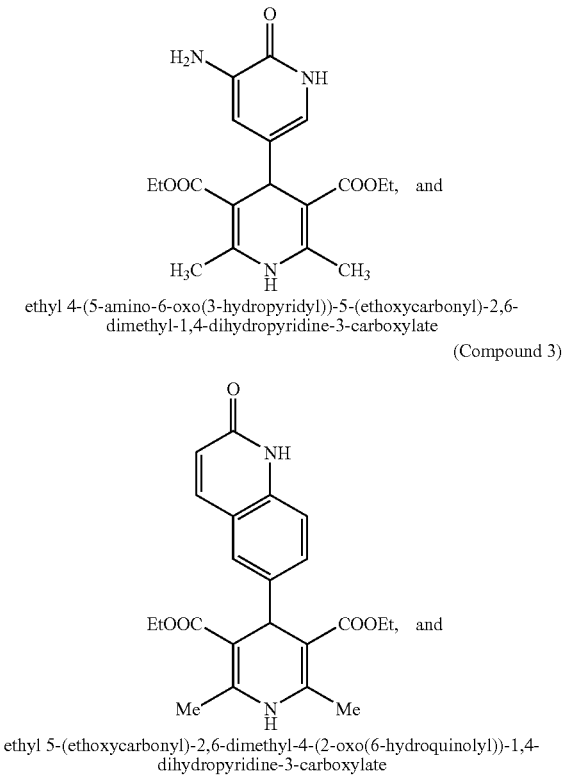

ethyl 4-(5-amino-6-oxo(3-hydropyridyl))-5-(ethoxycarbonyl)-2,6-dimethyl-1,4-dihydropyridine-3-carboxylate (Compound 3)

ethyl 5-(ethoxycarbonyl)-2,6-dimethyl-4-(2-oxo(6-hydroquinolyl))-1,4-dihydropyridine-3-carboxylate (Compound 4)

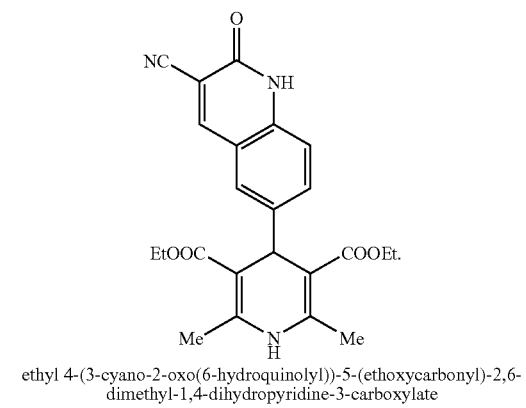

ethyl 4-(3-cyano-2-oxo(6-hydroquinolyl))-5-(ethoxycarbonyl)-2,6-dimethyl-1,4-dihydropyridine-3-carboxylate Another embodiment of the present invention encompasses a compound of formula II

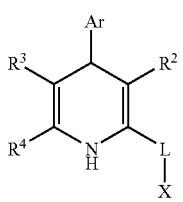

II or a pharmaceutically acceptable equivalent, an isomer or a mixture of isomers thereof, wherein:

$R^2$, $R^3$, $R^4$, L and X are as defined above; and

Ar is an aryl or heteroaryl that is optionally substituted in 1 to 3 position(s) with halo, nitro, cyano, trifluoromethyl, amino, —$NR^5R^6$, $C_1$–$C_4$ alkoxy, $C_1$–$C_4$ alkylthio, —$COOR^7$, $C_1$–$C_8$ alkyl, $C_2$–$C_8$ alkenyl or $C_2$–$C_8$ alkynyl, wherein one or more —$CH_2$— group(s) of the alkyl, alkenyl or alkynyl is/are optionally replaced with —O—, —S—, —$SO_2$— and/or —$NR^5$—, and the alkyl, alkenyl or alkynyl is optionally substituted with one or more carbonyl oxygen(s) and/or hydroxyl(s).

In one embodiment of formula II, when $R^2$ is —$COOCH_2CH_3$, $R^3$ is cyano, $R^4$ is methyl, L is methylene, X is a moiety of formula A, each R is hydrogen, and Ar is trifluoromethylphenyl, then L is not connected to the nitrogen atom of A; when $R^2$ and $R^3$ are each cyano, $R^4$ is amino, L is —$SCH_2$—, X is a moiety of formula P, and each R is hydrogen, then Ar is not fluorophenyl; and when $R^2$ is —$COOCH_2CH_3$, $R^3$ is —$COOCH_3$, $R^4$ is methyl, X is a moiety of formula P, each R is hydrogen, and Ar is chlorophenyl, then L is not —$CH_2OCH_2CH_2$—, —$CH_2OCH_2CH_2NHCO$— or —$CH_2OCH_2CH_2NCH_3CO$—.

In another embodiment of formula II, $R^2$ and $R^3$ are each —$COOR^7$, $R^4$ is $C_1$–$C_4$ alkyl, X is a moiety of formula A, and Ar is phenyl that is optionally substituted in 1 to 3 position(s).

Examples of compounds of formula II include without limitation:

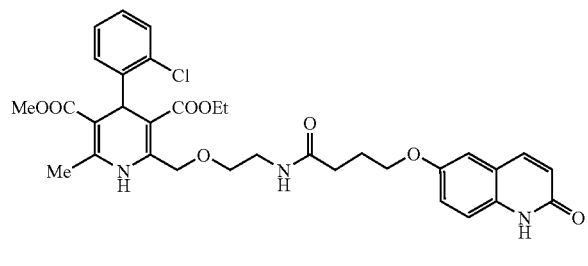

methyl 4-(2-chlorophenyl)-5-(ethoxycarbonyl)-2-methyl-6-({2-[4-(2-oxo(6-hydroquinolyloxy))butanoylamino]ethoxy}methyl)-1,4-dihydropyridine-3-carboxylate (Compound 5),

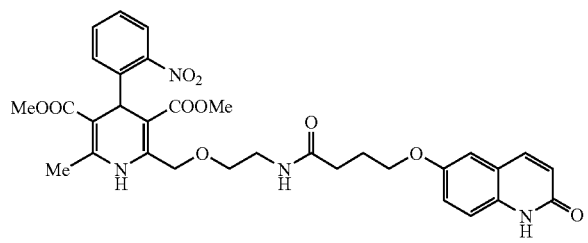

methyl 5-(methoxycarbonyl)-2-methyl-4-(2-nitrophenyl)-6-({2-[4-(2-oxo(6-hydroquinolyloxy))butanoylamino]ethoxy}methyl)-1,4-dihydropyridine-3-carboxylate (Compound 6),

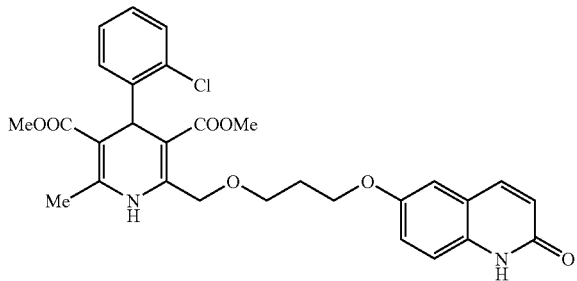

methyl 4-(2-chlorophenyl)-5-(methoxycarbonyl)-2-methyl-6-{[3-(2-oxo(6-hydroquinolyloxy))propoxy]methyl}-1,4-dihydropyridine-3-carboxylate (Compound 7),

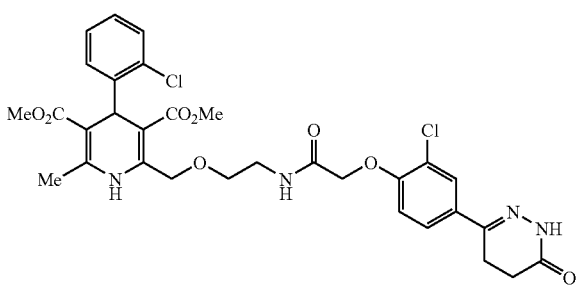

methyl 6-[(2-{2-[2-chloro-4-(6-oxo(1,4,5-trihydropyridazin-3-yl))phenoxy]acetylamino}ethoxy)methyl]-4-(2-chlorophenyl)-5-(methoxycarbonyl)-2-methyl-1,4-dihydropyridine-3-carboxylate (Compound 8),

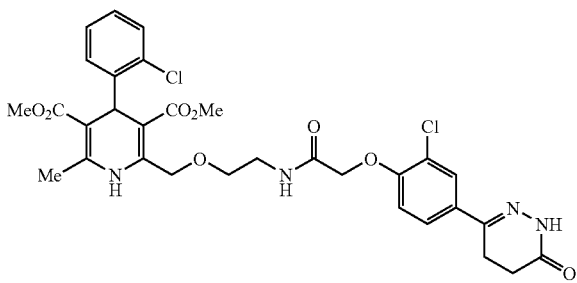

methyl 6-[(2-{2-[2-chloro-4-(6-oxo(1,4,5-trihydropyridazin-3-yl))phenoxy]acetylamino}ethoxy)methyl]-4-(2-chlorophenyl)-5-(ethoxycarbonyl)-2-methyl-1,4-dihydropyridine-3-carboxylate (Compound 9),

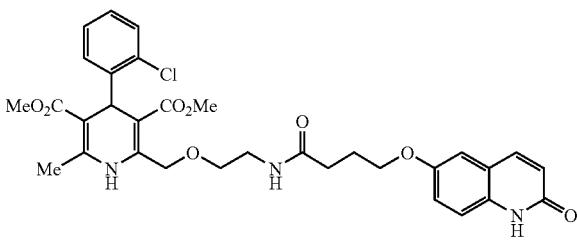

methyl 4-(2-chlorophenyl)-5-(methoxycarbonyl)-2-methyl-6-({2-[4-(2-oxo(6-hydroquinolyloxy))butanoylamino]ethoxy}methyl)-1,4-dihydropyridine-3-carboxylate (Compound 10),

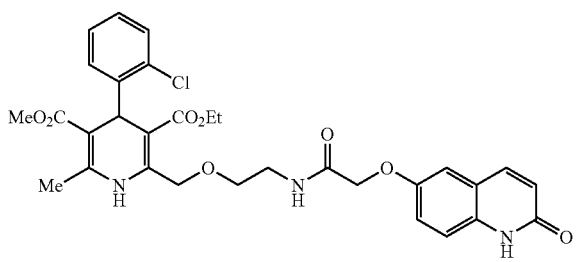

methyl 4-(2-chlorophenyl)-5-(ethoxycarbonyl)-2-methyl-6-({2-[2-(2-oxo(6-hydroquinolyloxy))acetylamino]ethoxy}methyl)-1,4-dihydropyridine-3-carboxylate (Compound 11),

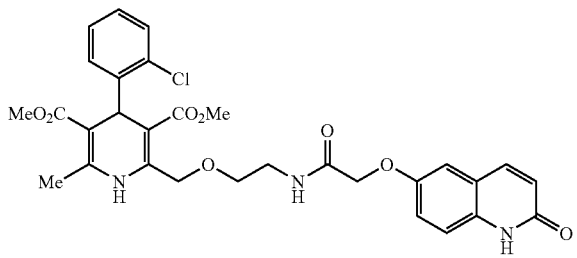

methyl 4-(2-chlorophenyl)-5-(methoxycarbonyl)-2-methyl-6-({2-[2-(2-oxo(6-hydroquinolyloxy))acetylamino]ethoxy}methyl)-1,4-dihydropyridine-3-carboxylate (Compound 12), and

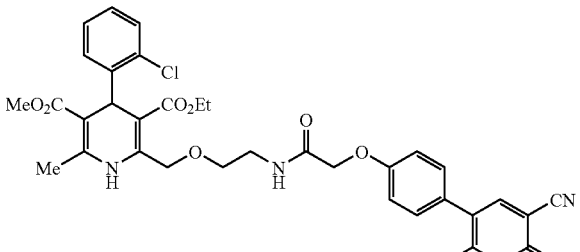

methyl 4-(2-chlorophenyl)-6-[(2-{2-[4-(5-cyano-2-methyl-6-oxo(3-hydropyridyl))phenoxy]acetylamino}ethoxy)methyl]-5-(ethoxycarbonyl)-2-methyl-1,4-dihydropyridine-3-carboxylate (Compound 13).

Another embodiment of the present invention encompasses a compound of formula III

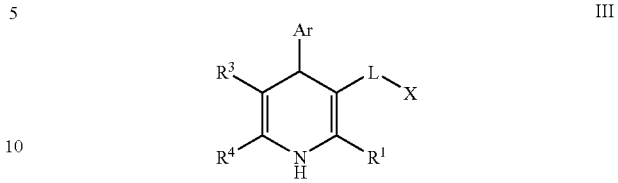

or a pharmaceutically acceptable equivalent, an isomer or a mixture of isomers thereof, wherein:

$R^1$, $R^3$, $R^4$, L, X and Ar are as defined above.

In one embodiment of formula III, when $R^1$ and $R^4$ are each methyl, $R^3$ is —COOCH$_3$, and X is a moiety of formula A or O, then L is not alkyl substituted with —COO— connected directly to the pyridine ring.

In another embodiment of formula III, $R^1$ and $R^4$ are each $C_1$–$C_4$ alkyl, $R^3$ is —COOR$^7$, X is a moiety of formula E, and Ar is phenyl that is optionally substituted in 1 to 3 position(s).

Examples of compounds of formula III include without limitation:

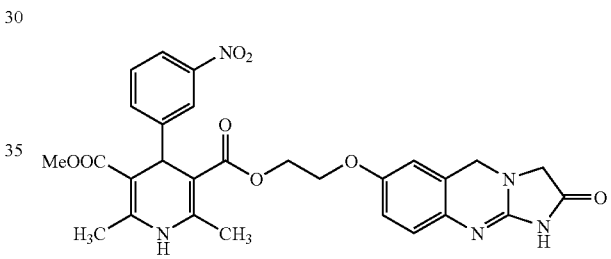

2-(2-oxo-4,3a-dihydroimidazolidino[2,1-b]quinazolin-6-yloxy)ethyl 5-(methoxycarbonyl)-2,6-dimethyl-4-(3-nitrophenyl)-1,4-dihydropyridine-3-carboxylate (Compound 14), and

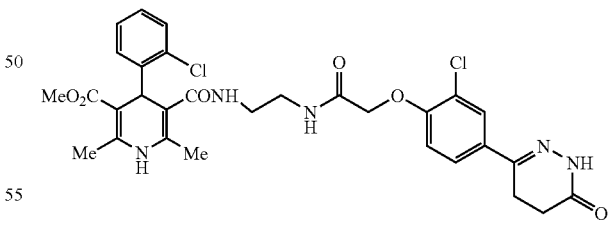

methyl 4-(2-chlorophenyl)-2,6-dimethyl-5-[N-(2-{2-[4-(6-oxo(1,4,5-trihydropyridazin-3-yl))phenoxy]acetylamino}ethyl)carbamoyl]-1,4-dihydropyridine-3-carboxylate (Compound 15).

Every variable substituent is defined independently at each occurrence. Thus, the definition of a variable substituent in one part of a formula is independent of its definition(s) elsewhere in that formula and of its definition(s) in other formulas.

Since the inventive compounds may possess one or more asymmetric carbon center(s), they may be capable of existing in the form of optical isomers as well as in the form of racemic or non-racemic mixtures of optical isomers. The optical isomers can be obtained by resolution of the racemic mixtures according to conventional processes. One such process entails formation of diastereoisomeric salts by treatment with an optically active acid or base, then separation of the mixture of diastereoisomers by crystallization, followed by liberation of the optically active bases from the salts. Examples of appropriate acids are tartaric, diacetyltartaric, dibenzoyltartaric, ditoluoyltartaric and camphorsulfonic acid.

A different process for separating optical isomers involves the use of a chiral chromatography column optimally chosen to maximize the separation of the enantiomers. Still another available process involves synthesis of covalent diastereoisomeric molecules, for example, esters, amides, acetals and ketals, by reacting the inventive compounds with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the "parent" optically active drug is not necessary prior to dosing the patient, since the compound can behave as a prodrug. The optically active compounds of this invention likewise can be obtained by utilizing optically active starting materials.

The compounds of this invention encompass individual optical isomers as well as racemic and non-racemic mixtures. In some non-racemic mixtures, the R configuration may be enriched while in other non-racemic mixtures, the S configuration may be enriched.

Methods of Treatment

This invention further provides a method for regulating calcium homeostasis, comprising administering an effective amount of an inventive compound to an animal in need of such regulation.

This invention further provides a method for treating a disease, disorder or condition in which disregulation of calcium homeostasis is implicated, comprising administering an effective amount of an inventive compound to an animal in need of such treatment.

This invention further provides a method for treating a cardiovascular disease, stroke, epilepsy, an ophthalmic disorder or migraine, comprising administering an effective amount of an inventive compound to an animal in need of such treatment.

In one embodiment of the inventive method, the cardiovascular disease is heart failure, hypertension, SA/AV node disturbance, arrhythmia, hypertrophic subaortic stenosis or angina. In another embodiment, the heart failure is chronic heart failure or congestive heart failure.

The inventive compound may be administered by any means known to an ordinarily skilled artisan. For example, the inventive compound may be administered orally, parenterally, by inhalation spray, topically, rectally, nasally, buccally, vaginally, or via an implanted reservoir. The term "parenteral" as used herein includes subcutaneous, intravenous, intramuscular, intraperitoneal, intrathecal, intraventricular, intrasternal, intracranial, and intraosseous injection and infusion techniques. The exact administration protocol will vary depending upon various factors including the age, body weight, general health, sex and diet of the patient; the determination of specific administration procedures would be routine to an ordinarily skilled artisan.

The inventive compound may be administered by a single dose, multiple discrete doses or continuous infusion. Pump means, particularly subcutaneous pump means, are useful for continuous infusion.

Dose levels on the order of about 0.001 mg/kg/d to about 10,000 mg/kg/d of the inventive compound are useful. In one embodiment, the dose level is about 0.1 mg/kg/d to about 1,000 mg/kg/d. In another embodiment, the dose level is about 1 mg/kg/d to about 100 mg/kg/d. The specific dose level for any particular patient will vary depending upon various factors, including the activity and the possible toxicity of the specific compound employed; the age, body weight, general health, sex and diet of the patient; the time of administration; the rate of excretion; the drug combination; the severity of the congestive heart failure; and the form of administration. Typically, in vitro dosage-effect results provide useful guidance on the proper doses for patient administration. Studies in animal models are also helpful. The considerations for determining the proper dose levels are well known in the art and within the skill of a physician.

Any administration regimen well known to an ordinarily skilled artisan for regulating the timing and sequence of drug delivery can be used and repeated as necessary to effect treatment in the inventive method. The regimen may include pretreatment and/or co-administration with additional therapeutic agent(s).

The compound of the present invention can be administered alone or in combination with one or more additional therapeutic agent(s) for simultaneous, separate, or sequential use. The additional agent(s) may be any therapeutic agent(s), including without limitation one or more compound(s) of the present invention. The compound of the present invention can be co-administered with one or more therapeutic agent(s) either (i) together in a single formulation, or (ii) separately in individual formulations designed for optimal release rates of their respective active agent.

Pharmaceutical Compositions

This invention further provides a pharmaceutical composition comprising:

(i) an effective amount of an inventive compound; and (ii) a pharmaceutically acceptable carrier.

The inventive pharmaceutical composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and additional therapeutic agent(s).

The inventive pharmaceutical composition may be formulated for administration in solid or liquid form, including those adapted for the following: (1) oral administration, for example, drenches (for example, aqueous or non-aqueous solutions or suspensions), tablets (for example, those targeted for buccal, sublingual and systemic absorption), boluses, powders, granules, pastes for application to the tongue, hard gelatin capsules, soft gelatin capsules, mouth sprays, emulsions and microemulsions; (2) parenteral administration, for example, by subcutaneous, intramuscular, intravenous or epidural injection as, for example, a sterile solution or suspension or a sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

EXAMPLES

Synthesis of Compounds

As shown in Scheme I below, dihydropyridines can be made by variations of Hantzsch chemistry, through the three component reaction of alkyl aminocrotonates with substituted benzaldehydes and β-ketoesters, or by reaction of benzylidene acetoacetates with aminocrotonates. Examples are found in Arrowsmith et al.; *J. Med. Chem.* 1986, 29, 1696–1702 and references contained therein, and Marciniak et al., *J. Med. Chem.* 1989, 32, 1402–1407 and references contained therein.

SCHEME I

-continued

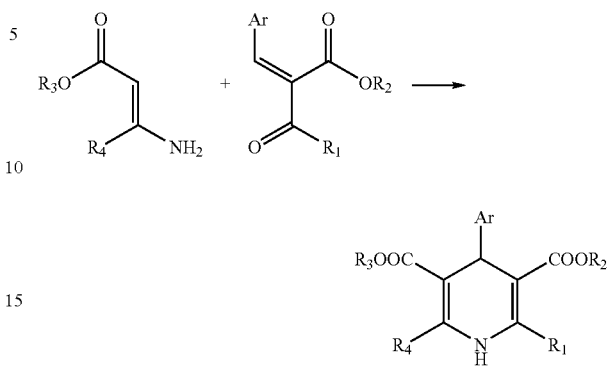

The dihydropyridines may be coupled with PDE-3 inhibitory moieties to produce the inventive compounds. The following examples are illustrative of the present invention and are not intended to be limitations thereon. Unless otherwise indicated, all percentages are based upon 100% by weight of the final composition.

Example 1

Methyl 4-(2-chlorophenyl)-5-ethoxycarbonyl)-2-methyl-6-({2-[4-(2-oxo(6-hydroquinolyloxy)butanoylamino]ethoxy}methyl-1,4-dihydropyridine-3-carboxylate (Compound 5) was synthesized according to Scheme II.

SCHEME II

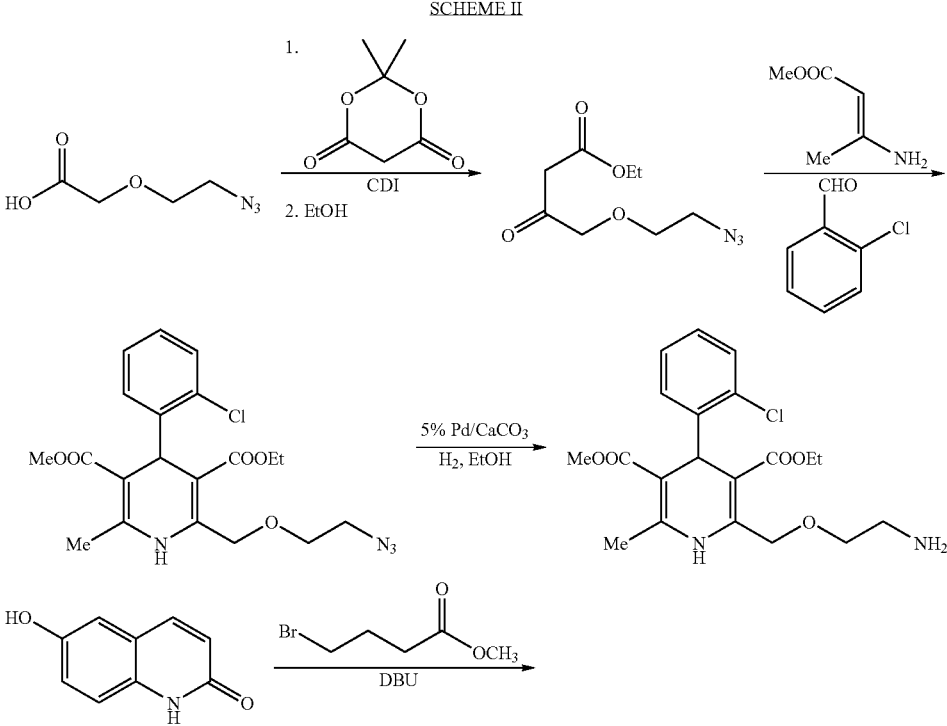

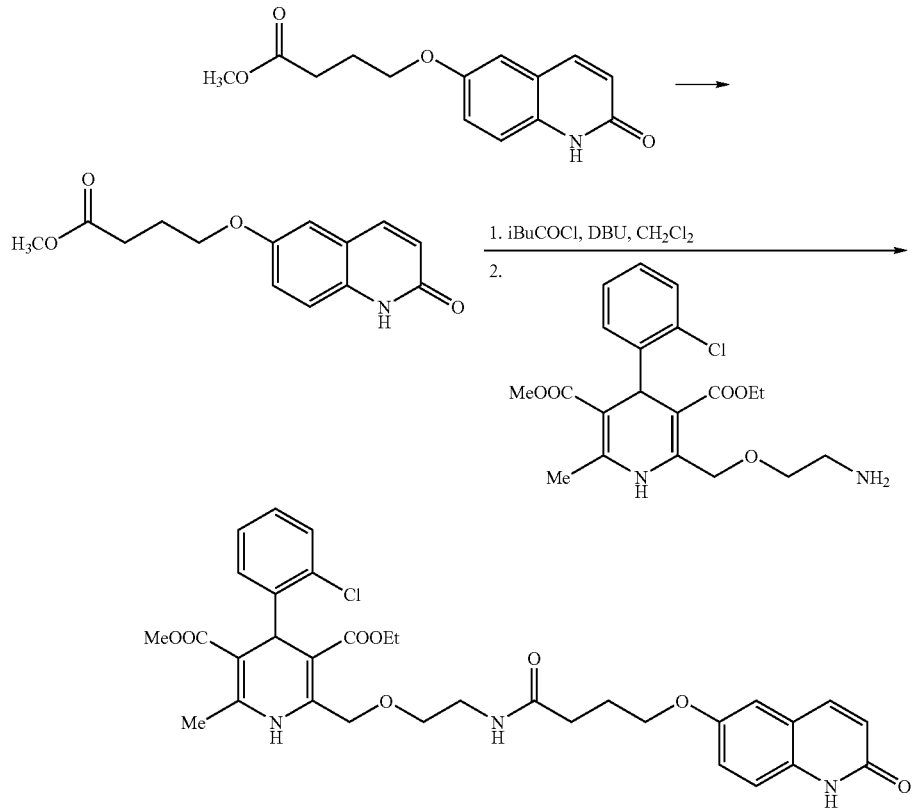

Methyl 4-(2-Azidoethoxy)-3-oxobutanoate: Carbonyldiimidazole (13.75 g; 0.084 mol) and 2-azidoethoxy acetic acid (11.0 g; 0.08 mol) [prepared by the method of Arrowsmith et al., *J. Med. Chem.* 1986, 29, 1696–1702] in 150 mL of methylene chloride was stirred under an inert atmosphere for 1 hour, and then treated with a solution of 2,2-dimethyl-1,3-dioxane-4,6-dione (11.0 g; 0.084 mol) and pyridine (6.1 g) in 50 mL of methylene chloride. After stirring overnight at room temperature, the organic phase was washed with 2×50 mL of 2M HCl, dried and concentrated. The crude material was dissolved in ethanol, refluxed for 3 hours, cooled and diluted with methylene chloride. The organic phase was washed with water, dried, and purified on a silica gel column (20% ethyl acetate in hexanes) to provide the keto ester as an oil, $^1$H NMR (400 MHz; CDCl$_3$): δ 4.53 (s, 2H); 4.12 (q, 2H); 3.45 (m, 2H); 3.41 (s, 2H); 1.50 (m, 2H); 1.30 (t, 3H).

2-[(2-azidoethoxy)methyl]-4-(2-chlorophenyl)-3-(ethoxycarbonyl)-5-(methoxycarbonyl)-6-methyl-1,4-dihydropyridine: A solution of the β-ketoester (7.0 g;), 2-chlorobenzaldehyde (4.0 g;) and methyl 3-aminocrotonate (3.3 g;) in ethanol (100 mL) was refluxed for 2 hours, then cooled, and the resulting precipitate was collected by filtration, washed with cold ethanol, and dried to furnish the dihydropyridine as a yellow solid, $^1$H NMR (400 MHz; CDCl$_3$): δ 7.15 (m, 1H); 7.02–7.00 (m, 3H); 4.43 (m, 1H); 4.19 (q, 2H); 4.04 (m, 2H); 3.76 (s, 3H); 3.42 (m, 2H); 1.71 (s, 3H); 1.53 (m, 2H); 1.30 (t, 3H).

2-[(aminoethoxy)methyl]-4-(2-chlorophenyl)-3-(ethoxycarbonyl)-5-(methoxycarbonyl-6-methyl-1,4-dihydropyridine: The azido dihydropyridine was hydrogenated at 15 psi in ethanol over 5% Pd/CaCO$_3$ catalyst. Filtration and concentration in vacuo delivered the amino compound as an oil, $^1$H NMR (400 MHz; CDCl$_3$): δ 7.15 (m, 1H); 7.02–7.00 (m, 3H); 4.43 (m, 1H); 4.20 (q, 2H); 4.02 (m, 2H); 3.75 (s, 3H); 3.63 (m, 2H); 2.82 (m, 2H); 1.71 (s, 3H); 1.31 (t, 3H).

Methyl 4-(2-oxo-6-hydroquinolyloxy)butanoate: Methyl 4-bromobutyrate (6.8 g) was added drop-wise with stirring to a solution of 5 g of 6-hydroxyhydroqionoline-2-one and 7 g of 1,8-diazabicyclo[5.4.0]undec-7-ene (DBU) in 75 mL of isopropanol, and refluxed for 4 hours. After cooling and removal of the solvent under vacuum, the residue was dissolved in methylene chloride and the organic phase was washed successively with 0.5N NaOH, diluted HCl and water, dried over MgSO$_4$, and concentrated. Re-crystallization of the crude product from water furnished the substituted quinolone as colorless needles, $^1$H NMR (400 MHz; CDCl$_3$): δ 7.48 (m, 1H); 7.36 (d, 1H); 6.79 (m, 1H); 6.63 (m, 1H); 6.57 (d, 1H); 3.94 (m, 2H); 3.67 (s, 3H); 2.25 (m, 2H); 2.10 (m, 2H).

4-(2-oxo-6-hydroquinolyl)butyric acid: A suspension of the methyl ester in 20% HCl was stirred for 2 hours at 90° C., cooled, and the crystals were collected by filtration, washed with cold water, and dried to deliver the acid as a granular solid, $^1$H NMR (400 MHz; CDCl$_3$): δ 7.48 (m, 1H); 7.36 (d, 1H); 6.79 (m, 1H); 6.63 (m, 1H); 6.57 (d, 1H); 3.94 (m, 2H); 2.23 (m, 2H); 1.98 (m, 2H).

Methyl 4-(2-chlorophenyl)-5-ethoxycarbonyl)-2-methyl-6-{2-[4-(2-oxo(6-hydroquinolyloxy)butanoylamino]ethoxy}methyl-1,4-dihydropyridine-3-carboxylate: Isobutyl chloroformate was added drop-wise to a solution of 4-(2-oxo-6-hydroquinolyl)butyric acid in methylene chloride, with stirring and in an ice bath at 0° C. The ice bath was removed and the mixture was stirred for 1 hour at room temperature, then treated with 0.9 eq. of 2-[(2-azidoethoxy)methyl]-4-(2-chlorophenyl)-3-(ethoxycarbonyl)-5-(methoxycarbonyl)-6-methyl-1,4-dihydropyridine and 1.1 eq. of triethylamine. After stirring the resulting mixture at room temperature for 3 hours, it was transferred to a separatory funnel, diluted with additional methylene chloride, and washed successively with 0.5 NaOH, diluted HCl and water, and dried over $MgSO_4$. After concentration in vacuo, the crude residue was purified on silica gel column to provide the final product, $^1$H NMR (400 MHz; $CDCl_3$): δ 7.48 (m, 1H); 7.36 (d, 1H); 7.15 (m, 1H); 7.02–7.00 (m, 3H); 6.79 (m, 1H); 6.63 (m, 1H); 6.57 (d, 1H); 4.43 (m, 1H); 4.19 (m, 2H); 4.04 (m, 2H); 3.94 (m, 2H); 3.76 (s, 3H); 3.63 (s, 2H); 3.37 (m, 2H); 2.18 (m, 2H); 1.99 (m, 2H); 1.71 (s, 3H); 1.30 (t, 3H).

Example 2

Methyl 5-(methoxycarbonyl)-2-methyl-4-(2-nitrophenyl)-6-({2-[4-2-oxo(6-hydroquinolyloxy)butanoylamino]ethoxy}methyl)-1,4-dihydropyridine-3-carboxylate (Compound 6) was synthesized according to Scheme II. $^1$H NMR (400 MHz; $CDCl_3$): δ 8.07 (m, 1H); 7.53 (m, 1H); 7.48 (m, 1H); 7.36 (d, 1H); 7.33 (m, 1H); 7.32 (m, 1H); 6.79 (m, 1H); 6.63 (m, 1H); 6.57 (d, 1H); 4.43 (m, 1H); 4.04 (m, 2H); 3.94 (m, 2H); 3.76 (s, 6H total); 3.63 (m, 2H); 3.37 (M, 2H); 2.18 (m, 2H); 1.99 (m, 2H); 1.71 (s, 3H).

Example 3

Methyl 4-(2-chlorophenyl)-5-(methoxycarbonyl)-2-methyl-6-{[3-(2-oxo(6-hydroquinolyloxy))propoxy]methyl}-1,4-dihydropyridine-3-carboxylate (Compound 7) was synthesized according to Scheme III.

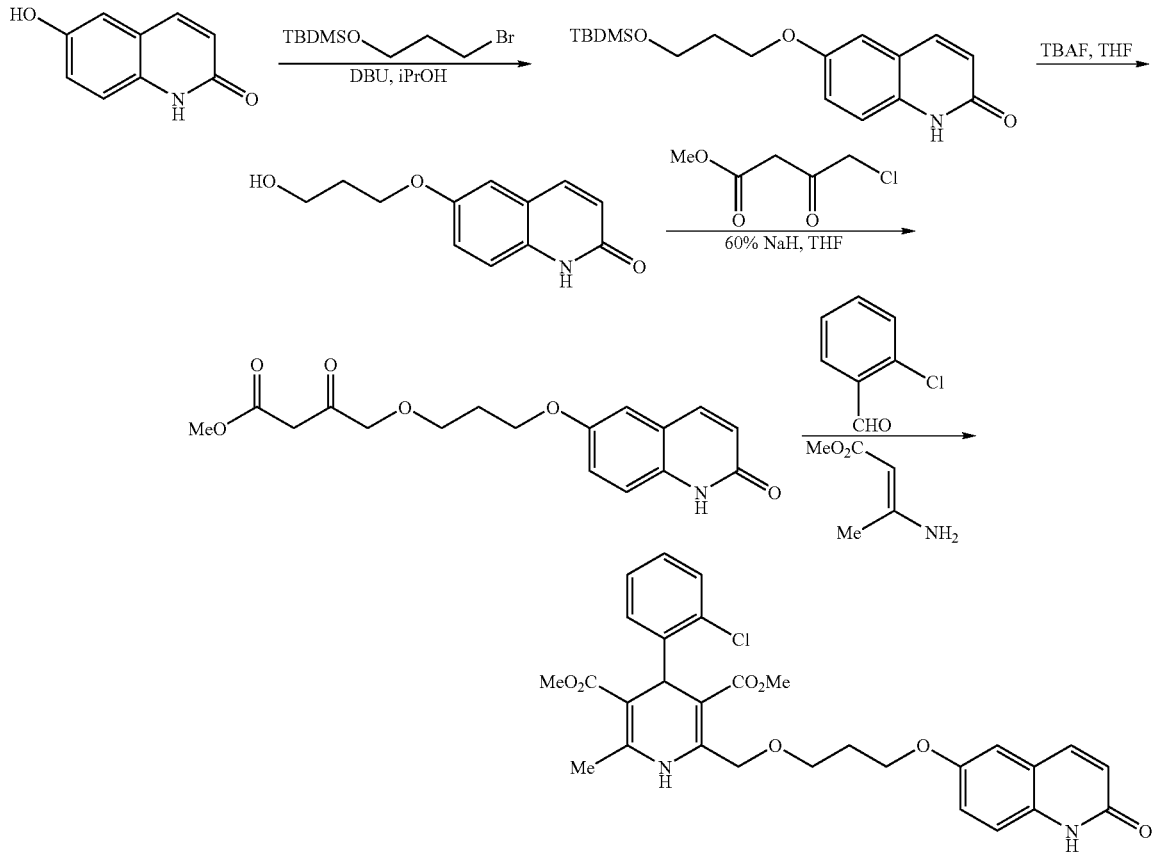

SCHEME III

6-[3-(1,1,2,2-tetramethyl-1-silapropoxy)propoxy]hydroquinolin-2-one: (3-Bromopropxyl)-tert-butyldimethylsilane (1.63 g, 1.50 mL, 6.5 mmol) was added drop-wise into a mixture of 6-hydroxyhydroquinolin-2-one (1.04 g, 6.5 mmol), DBU (1.73 g, 1.70 mL, 11.38 mmol) in isopropanol (20 mL). The mixture was refluxed for 21 hours and cooled to room temperature and evaporated to remove the solvent. The residue was extracted with ethyl acetate (EtOAc; 150 mL) and the extracts were washed with water, dried over $Na_2SO_4$, and filtered. The filtrate was concentrated to give the product as an off-white solid (1.6 g, 76%), $^1$H NMR (400 MHz; $CDCl_3$): δ 7.48 (m, 1H); 7.36 (d, 1H); 6.79 (m, 1H); 6.63 (m, 1H); 6.57 (d, 1H); 3.94 (m, 2H); 3.79 (m, 2H); 1.90 (m, 2H); 1.00–0.08 (overlapping singlets, 15H total).

6-(3-hydroxypropoxy)hydroquinolin-2-one: To a solution of 6-[3-(1,1,2,2-tetramethyl-1-silapropoxy)propoxy]hydroquinolin-2-one (1.50 g, 4.5 mmol) in tetrahydrofuran (THF; 20 mL) was added drop-wise a solution of 1.0 M tetrabutylammonium fluoride in THF at 0° C. and the mixture was stirred for 10 minutes at 0° C. and at room temperature for 1.5 hours. Aqueous saturated NH$_4$Cl was added into the reaction solution and the solvent was removed by evaporation. The residue was partitioned with 40 mL of EtOAc and water (40 mL) and filtered to remove the solid. The solid was washed with water and then 50% EtOAc/hexane to give the product as an off-white solid (581 mg 59%), $^1$H NMR (400 MHz; CDCl$_3$): δ 7.48 (m, 1H); 7.36 (d, 1H); 6.79 (m, 1H); 6.63 (m, 1H); 6.57 (d, 1H); 3.94 (m, 2H); 3.53 (m, 2H); 1.90 (m, 2H).

Methyl 3-oxo-4-[3-(2-oxo(6-hydroquinolyloxy))propoxy]butanoate: A suspension of the alcohol from the previous step (573 mg, 2.61 mmol) in THF (15 mL) was added in portion wise into a suspension of 60% NaH (209 mg, 5.22 mmol) in 10 ml of THF and then a solution of methyl 4-chloroacetoacetate (393 mg, 0.3 mL, 2.61 mmol) in THF (5 mL). The mixture was stirred at room temperature overnight. Thin layer chromatography (TLC) showed no reaction. Dimethylformamide (DMF) (1.0 mL) and 60% NaH (203 mg, 5.22 mmol) were successively added and the mixture was stirred at room temperature for 2 days. The solvents were removed by evaporation to give a residue, which was treated with 10% acetic acid (HOAc; 10 mL) and extracted with EtOAc (30 mL×5) and the combined organic layers were dried over Na$_2$SO$_4$, and filtered. The filtrate was concentrated to give a residue, which was purified by column chromatography with hexane-50% EtOAc/hexane-EtOAc-10% MeOH/EtOAc to afford the product as a yellow-white solid (361 mg, 42%), $^1$H NMR (400 MHz; CDCl$_3$): δ 7.48 (m, 1H); 7.35 (d, 1H); 6.77 (m, 1H); 6.63 (m, 1H); 6.58 (d, 1H); 4.53 (m, 2H); 3.94 (m, 2H); 3.67 (s, 3H); 3.41 (s, 2H); 3.37 (m, 2H); 1.88 (m, 2H).

Methyl 4-(2-chlorophenyl)-5-(methoxycarbonyl)-2-methyl-6-{[3-(2-oxo(6-hydroxy-quinolyloxy)propoxy]methyl}-1,4-dihydropyridine-3-carboxylate (Example III): A solution of 2-chlorobenzaldehyde (197 mg, 1.4 mmol), methyl 3-aminocrotonate (161 mg, 1.4 mmol), methyl 3-oxo-4-[3-(2-oxo(6-hydroquinolyloxy))propoxy]butanoate (424 mg, 1.27 mmol) in thanol (10 mL) was refluxed overnight and cooled to room temperature. The solvents were removed by evaporation to give a residue, which was purified by column chromatography with CH$_2$Cl$_2$-10% MeOH/CH$_2$Cl$_2$ to afford the product (70 mg, 10%), $^1$H NMR (400 MHz; CDCl$_3$): δ 7.48 (m, 1H); 7.36 (d, 1H); 7.15 (m, 1H); 7.02–7.00 (m, 3H); 6.79 (m, 1H); 6.63 (m, 1H); 6.57 (d, 1H); 4.43 (m, 1H); 4.04 (m, 1H); 3.94 (m, 2H); 3.76 (singlets, 6H total); 3.37 (m, 2H); 1.88 (m, 2H); 1.71 (s, 3H).

Example 4

2-(2-Oxo-4,3a-dihydroimidazolidino[2,1-b]quinazolin-6-yloxy)ethyl 5-(methoxycarbonyl)-2,6-dimethyl-4-(3-nitrophenyl)-1,4-dihydropyridine-3-carboxylate (Compound 14) is synthesized according to Scheme IV. The intermediate tetrahydro-2-oxoimidazo[2,1-b]quinazoline is prepared as described by Venuti et al., *J. Med. Chem.* 1988, 31, 2136–2145.

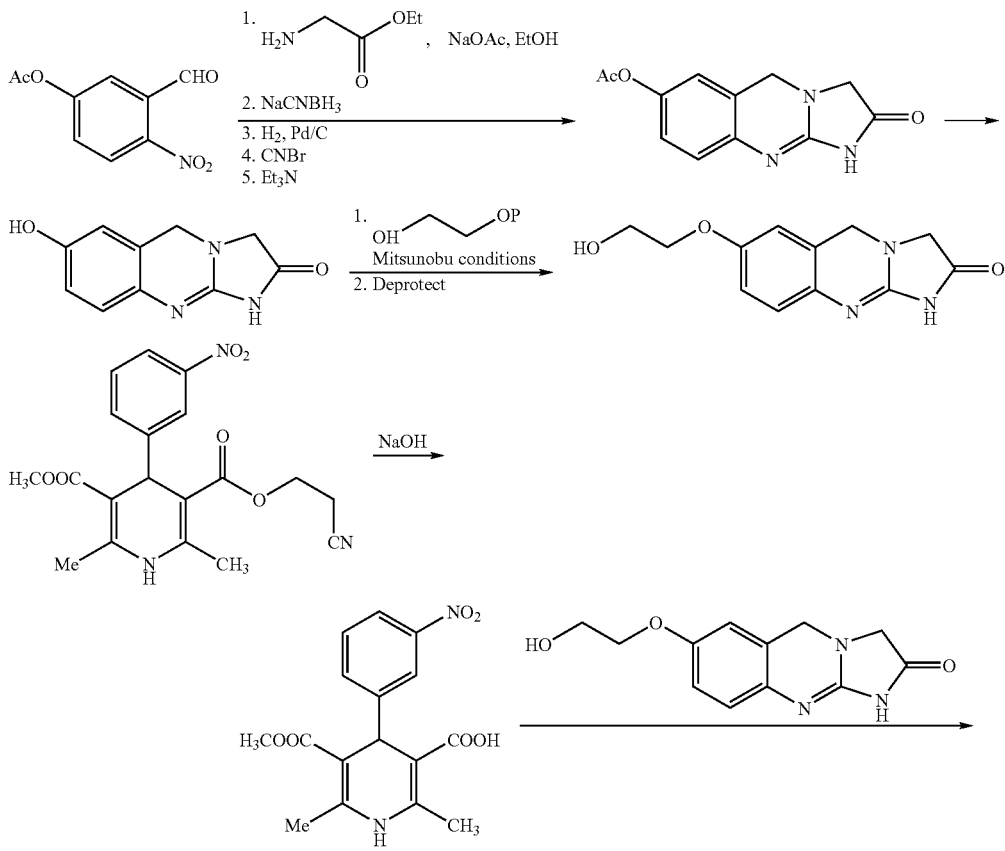

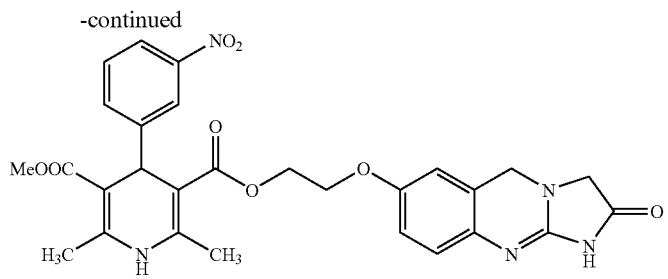

Example 5

Methyl 6-[(2-{2-[2-chloro-4-(6-oxo(1,4,5-trihydropyridazin-3-yl))phenoxy]acetylamino}ethoxy)methyl]-4-(2-chlorophenyl)-5-(methoxycarbonyl)-2-methyl-1,4-dihydropyridine-3-carboxylate (Compound 8) and methyl 6-[(2-{2-[2-chloro-4-(6-oxo(1,4,5-trihydropyridazin-3-yl))phenoxy]acetylamino}ethoxy)methyl]-4-(2-chlorophenyl)-5-(ethoxycarbonyl)-2-methyl-1,4-dihydropyridine-3-carboxylate (Compound 9) were synthesized according to Schemes V-a, -b and -c.

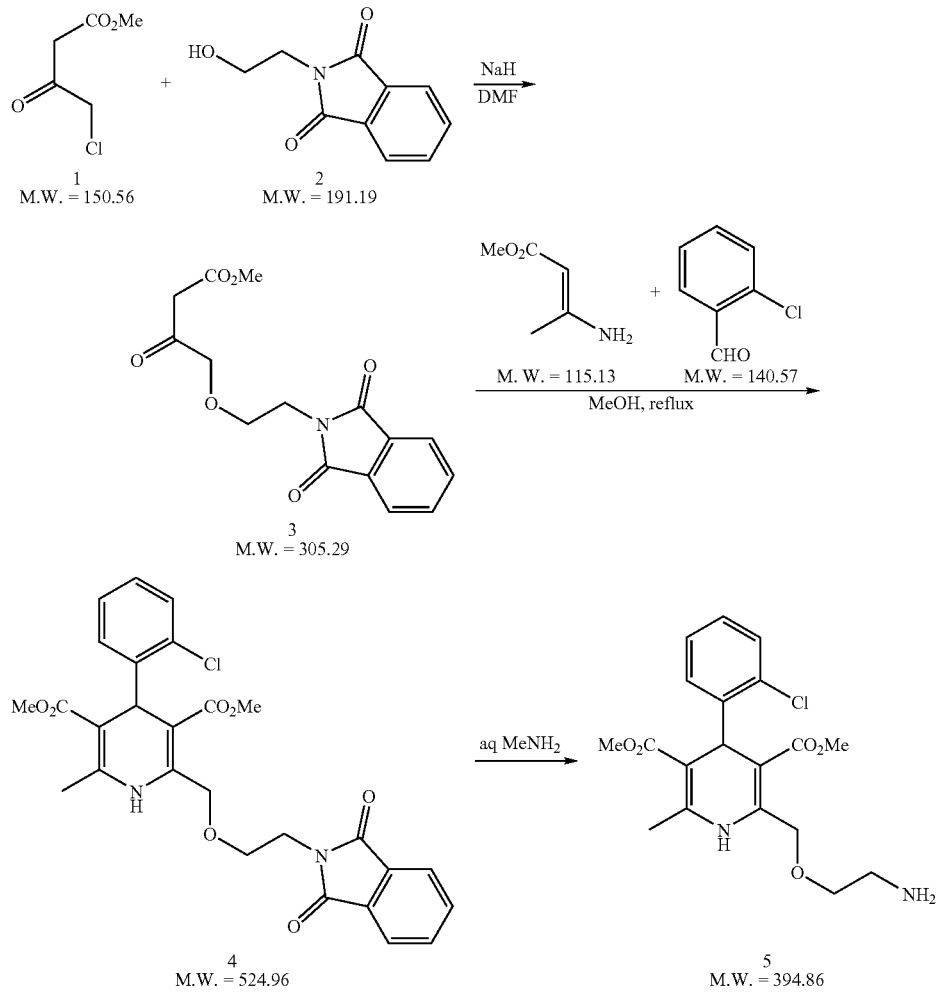

4-[2-(1,3-Dioxo-1,3-dihydro-isoindol-2-yl)-ethoxy]-3-oxo-butyric acid methyl ester (3): To a stirred suspension of sodium hydride (60% dispersion in mineral oil, 6.28 g, 157 mmol) in N,N-dimethylformamide (150 mL) under nitrogen at 0° C. was added portion wise N-(2-hydroxyethyl)phthalimide (2, 20 g, 105 mmol). The reaction mixture was then allowed to warm to ambient temperature with stirring for 30 minutes. To a stirred suspension in a separate flask of sodium hydride (60% dispersion in mineral oil, 6.28 g, 157 mmol) in N,N-dimethylformamide (150 mL) under nitrogen at 0° C. was added portion wise methyl 4-chloroacetoacetate (1, 12.1 ml, 105 mmol). The reaction mixture was then allowed to warm to ambient temperature with stirring for 30 minutes. The two reaction mixtures were then combined portion wise and stirred at ambient temperature under nitrogen for 6 hours. After cooling to 0° C., a further portion of sodium hydride (2.0 g, 50.0 mmol) was added. The mixture was stirred for 10 minutes at 0° C., then a further portion of methyl 4-chloroacetoacetate (3.0 ml, 26.0 mmol) was added. The reaction mixture was then stirred at ambient temperature for 18 hours, then poured onto a mixture of ice and saturated ammonium chloride, and then neutralized with aqueous HCl (10 N). The precipitate which formed was filtered off and re-crystallized from ethyl acetate to give a first crop of 3 as a yellow solid. The combined filtrates were extracted with ethyl acetate (3×300 mL). The combined organic layers were washed with saturated brine (2×300 mL) and water (300 mL), dried over MgSO₄ and concentrated under reduced pressure to leave a residue which was purified by column chromatography over silica gel (50 g pre-packed Isolute® column) using ethyl acetate/hexane (1:1) as eluent to give a second crop of 3 as a yellow solid, which was combined with the first crop to give methyl 4-((2'-hydroxyethyl)phthalimide)acetoacetate (3) (10.8 g, 34% yield, 95% pure by LCMS and ¹H NMR), ¹H NMR (400 MHz; CDCl₃): δ 8.13 (m, 2H); 7.69 (m, 2H); 4.53 (s, 2H); 3.80 (m, 2H); 3.70 (m, 2H); 3.67 (s, 3H); 3.41 (s, 2H).

4-(2-Chloro-phenyl)-2-[2-(1,3-dioxo-13-dihydro-isoindol-2-yl)-ethoxymethyl]-6-methyl-1,4-dihydro-pyridine-3,5-dicarboxylic acid dimethyl ester (dimethylamlodipine phthalimide)(4): To a stirred suspension of 4-[2-(1,3-dioxo-1,3-dihydro-isoindol-2-yl)-ethoxy]-3-oxo-butyric acid methyl ester (3, 10.8 g, 35.4 mmol) in methanol (250 mL) at ambient temperature were added 2-chlorobenzaldehyde (4.98 g, 35.4 mmol) and methyl 3-aminocrotonate (4.08 g, 35.4 mmol). The reaction mixture was then heated to reflux under nitrogen, then stirred at this temperature for 6 days until LCMS analysis indicated less than 5% starting material 3 remained. The mixture was then allowed to cool to ambient temperature and the precipitate which formed was filtered and dried under suction to give a first crop of light yellow solid. The filtrate was evaporated to dryness and the residue was re-crystallized from methanol to obtain a second crop of light yellow solid. The products of the two crops were combined, giving dimethylamlodipine phthalimide (4) as light yellow powder (8.3 g, 45% yield, 91% pure by LCMS and ¹H NMR), ¹H NMR (400 MHz; CDCl₃): δ 8.13 (m, 2H); 7.68 (m, 2H); 7.15 (m, 1H); 7.02–7.00 (m, 3H); 4.43 (m, 1H); 4.04 (s, 2H); 3.80 (m, 2H); 3.76 (singlets, 6H total); 3.70 (m, 2H); 1.71 (s, 3H).

2-(2-Amino-ethoxymethyl)-4-(2-chloro-phenyl)-6-methyl-1,4-dihydro-pyridine-3,5-dicarboxylic acid dimethyl ester (dimethylamlodipine)(5): To a stirred solution of methylamine (40 wt % in water, 125 mL, 1.45 mol) at ambient temperature was added 4-(2-chloro-phenyl)-2-[2-(1,3-dioxo-1,3-dihydro-isoindol-2-yl)-ethoxymethyl]-6-methyl-1,4-dihydro-pyridine-3,5-dicarboxylic acid dimethyl ester (dimethylamlodipine phthalimide) (4, 6.30 g, 12.0 mmol). The reaction mixture was stirred at ambient temperature for 18 hours, then diluted with water (100 mL) and extracted with ethyl acetate (3×100 mL). The combined organic extracts were washed with saturated brine (100 mL), dried over MgSO₄ and concentrated under reduced pressure to give 5 a yellow oil (4.0 g, 84% yield, 90% pure by LCMS and ¹H NMR), ¹H NMR (400 MHz; CDCl₃): δ 7.15 (m, 1H); 7.02–7.00 (m, 3H); 4.43 (m, 1H); 4.04 (s, 2H); 3.76 (singlets, 6H total); 3.63 (m, 2H); 2.82 (m, 2H); 1.71 (s, 3H).

SCHEME V-b
Synthesis of pyridazinone carboxylic acid
(as in EP 0178189, Morisawa et al, pages 80 and 81)

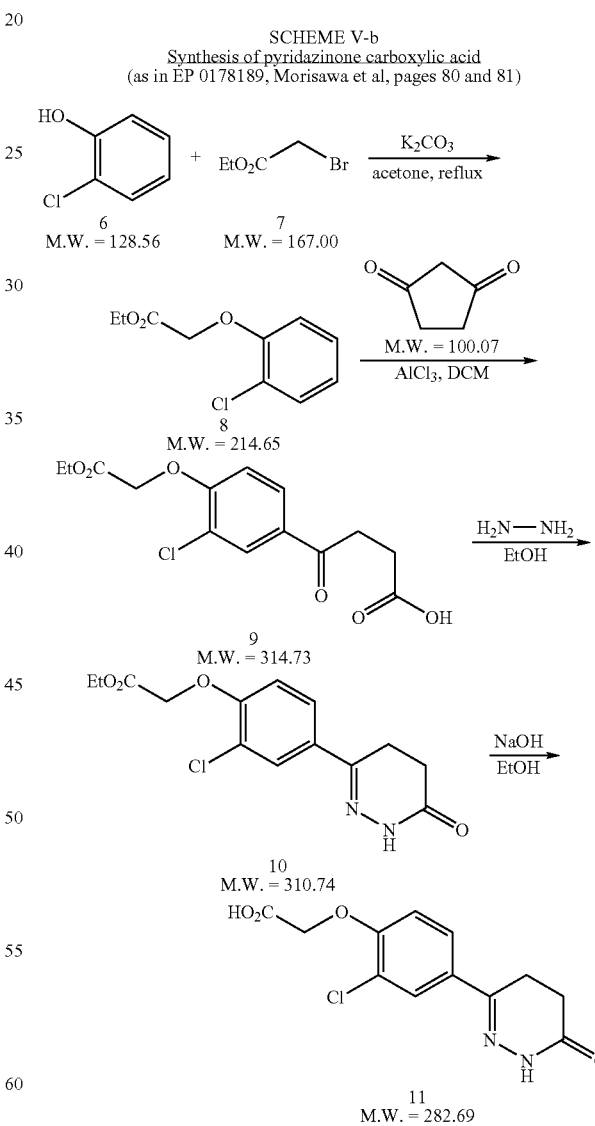

Ethyl 2-chlorophenoxyacetate (8): To a stirred solution of 2-chlorophenol (6, 20.0 g, 156 mmol) in acetone (300 mL) under nitrogen at ambient temperature were added potassium carbonate (23.7 g, 171 mmol) and ethyl bromoacetate (7, 26.0 g, 156 mmol). The reaction mixture was then heated to reflux and stirred at this temperature under nitrogen for 7 hours. After cooling to ambient temperature, the reaction mixture was filtered to remove insolubles. The filtrate was then concentrated under reduced pressure to give 8 as highly viscous, light yellow oil (32.0 g, 95% yield, 95% pure by LCMS and $^1$H NMR), $^1$H NMR (400 MHz; CDCl$_3$): δ 7.16 (m, 1H); 7.03 (m, 1H); 6.76 (m, 1H); 6.71 (m, 1H); 4.90 (s, 2H); 4.12 (q, 2H); 1.33 (t, 3H).

4-[3-Chloro-4-(ethoxycarbonylmethoxy)phenyl]-4-oxobutyric acid (9): To a stirred solution of ethyl 2-chlorophenoxyacetate (32.0 g, 149 mmol) in dichloromethane (75 mL) at ambient temperature under nitrogen was added succinic anhydride (22.4 g, 224 mmol). The reaction mixture was cooled in ice-water and to this was added portion wise aluminum trichloride (59.6 g, 447 mmol), whilst maintaining the temperature below 20° C. The reaction mixture was then allowed to stir at ambient temperature for 20 minutes and was then heated to reflux and stirred at this temperature for 3 hours. The reaction mixture was allowed to cool to ambient temperature, then poured into a mixture of ice, water (200 ml) and HCl (10 N, 100 ml). The two phase system was separated and the aqueous layer was extracted with ethyl acetate (5×100 mL). All organic layers were then combined and washed with water (2×100 mL), dried over Na$_2$SO$_4$, and concentrated under reduced pressure to give an orange oily solid. Hexane (300 mL) was added, and after standing at ambient temperature for 1 hour, the precipitate was filtered off and re-crystallized from ethyl acetate/hexane to give 9 as a light yellow powder (21.5 g, 46% yield, 98% pure by LCMS and $^1$H NMR), $^1$H NMR (400 MHz; CDCl$_3$): δ 7.79 (m, 1H); 7.66 (m, 1H); 6.79 (m, 1H); 4.90 (s, 2H); 4.12 (q, 2H); 2.82 (m, 2H); 2.42 (m, 2H); 1.30 (t, 3H).

6-[3-Chloro-4-(ethoxycarbonylmethoxy)phenyl]-4,5-dihydro-3 (2H)-pyridazinone (10): To a stirred suspension of 4-[3-chloro-4-(ethoxycarbonylmethoxy)phenyl]-4-oxobutyric acid (9, 21.5 g, 69.2 mmol) in ethanol (200 mL) at 0° C. was added a solution of hydrazine monohydrate (3.4 mL, 69.2 mmol) in ethanol (20 mL). The reaction mixture was then allowed to warm to ambient temperature and stirred at this temperature for 15 minutes before being heated to reflux and stirred at this temperature for 3 hours. Ethyl acetate (40 mL) was added to the hot solution and the mixture was allowed to cool to ambient temperature. The precipitate which formed was filtered off and washed with water (2×100 mL) and cold ethanol (2×100 mL), then dried with suction, then under high vacuum to give 10 as light yellow powder (17.6 g, 82% yield, 99% pure by LCMS and $^1$H NMR), $^1$H NMR (400 MHz; CDCl$_3$): δ 7.52 (m, 1H); 7.41 (m, 1H); 6.70 (m, 1H); 4.90 (s, 2H); 4.12 (q, 2H); 2.22 (m, 2H); 1.62 (m, 2H); 1.30 (q, 3H).

Pyridazinone carboxylic acid (6-[4-[3-carboxymethoxy]-3-chlorophenyl]-4,5-dihydro-3(2H)-pyridazinone) (11): To a stirred suspension of 6-[3-chloro-4-(ethoxycarbonyl-methoxy)phenyl]-4,5-dihydro-3(2H)-pyridazinone (10, 17.6 g, 56.6 mmol) in ethanol (150 mL) at ambient temperature were added water (150 mL) and sodium hydroxide (9.10 g, 227 mmol). The reaction mixture was then heated to 80° C. and stirred at this temperature for 2.5 hours. The solution was allowed to cool until precipitation occurred, then the suspension was acidified to pH 1-2 with HCl (2 N, 100 mL) with stirring. After standing at ambient temperature for 1 hour, the precipitate was filtered off and washed with water (2×100 mL) and ethanol (2×100 mL). The solid was dried under high vacuum at 45° C. to give 6-{4-[3-carboxymethoxy]-3-chlorophenyl}-4,5-dihydro-3(2H)-pyridazinone (11) as a light yellow powder (13.4 g, 84% yield, 99% pure by LCMS and $^1$H NMR), $^1$H NMR (400 MHz; CDCl$_3$): δ 7.52 (m, 1H); 7.44 (m, 1H); 6.72 (m, 1H); 4.88 (s, 2H); 2.21 (m, 2H); 1.61 (m, 2H).

SCHEME V-c
Final coupling reactions

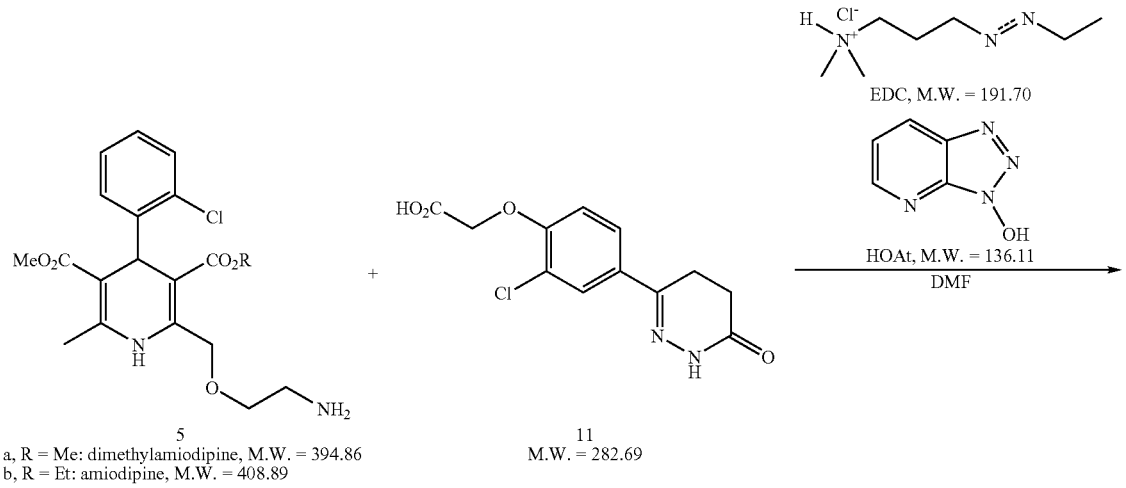

-continued

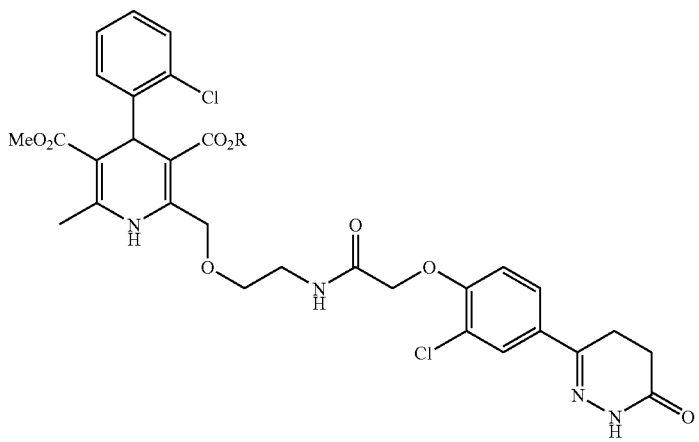

12
a, R = Me (ATI-107): M.W. = 659.53
b, R = Et (ATI-108): M.W. = 673.56

2-(2-{2-[2-Chloro-4-(6-oxo-1,4,5,6-tetrahydro-pyridazin-3-yl)-phenoxy]-acetylamino}-ethoxymethyl)-4-(2-chloro-phenyl)-6-methyl-1,4-dihydro-pyridine-3,5-dicarboxylic acid dimethyl ester (Compound 8): 6-{4-[3-Carboxymethoxy]-3-chlorophenyl}-4,5-dihydro-3(2H)-pyridazinone (11, 1.38 g, 4.88 mmol), 1-(3-dimethylaminopropyl)-3-ethyl carbodiimide hydrochloride (0.935 g, 4.88 mmol) and 7-hydroxyazabenzotriazole (0.265 g, 1.95 mmol) were mixed as solids. N,N-dimethylformamide (70 mL) was then added and the mixture was sonicated at ambient temperature for 5 minutes to give a homogeneous, light yellow solution. A solution of 2-(2-amino-ethoxymethyl)-4-(2-chloro-phenyl)-6-methyl-1,4-dihydro-pyridine-3,5-dicarboxylic acid dimethyl ester (dimethylamlodipine) (5a, 1.93 g, 4.88 mmol) in N,N-dimethylformamide (30 mL) was added and the reaction mixture was stirred at ambient temperature for 18 hours. Ethyl acetate (100 mL) and water (120 mL) were then added and the mixture was extracted with ethyl acetate (3×100 mL). The combined organic layers were washed with aqueous sodium hydroxide solution (2 N, 100 mL) and brine (2×100 mL), dried over MgSO$_4$ and concentrated under reduced pressure to give yellow solid which was re-crystallized from ethyl acetate/diethyl ether to obtain a first crop of Compound 8 (12a). The mother liquors were taken and concentrated under reduced pressure and the solid was purified by flash column chromatography over silica gel (20 g) using ethyl acetate as eluent. The combined fractions were concentrated under reduced pressure and the solid obtained was re-crystallized from ethyl acetate/diethyl ether to give a second crop of Compound 8 (12a) as light yellow powder, which was combined with the first crop product to give 2-(2-{2-[2-chloro-4-(6-oxo-1,4,5,6-tetrahydro-pyridazin-3-yl)-phenoxy]-acetylamino}-ethoxymethyl)-4-(2-chloro-phenyl)-6-methyl-1,4-dihydro-pyridine-3,5-dicarboxylic acid dimethyl ester (12a) as a light yellow powder (1.10 g, 34% yield, 99% pure by LCMS (UV @ 215 nm: retention time=6.15 min., peak area=99%, TOF-ES$^+$ with 25 eV cone voltage: m/z=659.05 (100%) & 661.02 (75%)). $^1$H NMR: (CDCl$_3$, TMS internal standard, δ in ppm): 8.55 (1H, s), 7.85 (1H, d, J=2.20 Hz), 7.59 (1H, dd, J=8.68 Hz, J2=2.32 Hz), 7.37 (1H, dd, J1=7.83 Hz, J2=1.71 Hz), 7.23 (1H, dd, J1=7.83 Hz, J2=1.22 Hz), 7.18 (1H, broad s), 7.13 (2H, td, J1=7.46 Hz, J2=1.22 Hz), 7.04 (1H, J=7.58 Hz, J2=1.71 Hz), 6.94 (1H, d, J=8.80 Hz), 5.41 (1H, s), 4.75 (1H, d, J=15.65 Hz), 4.67 (1H, d, J=15.89 Hz), 4.62 (2H, s), 3.78–3.63 (4H, m), 3.61 (3H, s), 3.59 (3H, s), 2.94 (2H, t, J=8.19 Hz), 2.61 (2H, t, J=8.19 Hz), 2.36 (3H, s).

2-(2-{2-[2-Chloro-4-(6-oxo-1,4,5,6-tetrahydro-pyridazin-3-yl)-phenoxy]-acetylamino}-ethoxymethyl)-4-(2-chloro-phenyl)-6-methyl-1,4-dihydro-pyridine-3,5-dicarboxylic acid 3-ethyl ester 5-methyl ester (Compound 9): 2-(2-{2-[2-Chloro-4-(6-oxo-1,4,5,6-tetrahydro-pyridazin-3-yl)-phenoxy]-acetylamino}-ethoxymethyl)-4-(2-chloro-phenyl)-6-methyl-1,4-dihydro-pyridine-3,5-dicarboxylic acid 3-ethyl ester 5-methyl ester (Compound 9) (12b) was synthesized from commercial amlodipine (5b, 1.73 g, 4.23 mmol) and 6-{4-[3-carboxymethoxy]-3-chlorophenyl}-4,5-dihydro-3(2H)-pyridazinone (11) using the same procedure as for Compound 8. Pure Compound 9 was obtained by re-crystallization from ethyl acetate (1.45 g, 51% yield, 99% pure by 10 min. LCMS (UV @ 215 nm: retention time=6.86 min., peak area=99%, TOF-ES$^+$ with 25 eV cone voltage: m/z=673.30 (100%) & 675.30 (30%)). $^1$H NMR: (CDCl$_3$, TMS internal standard, δ in ppm): 8.50 (1H, s), 7.85 (1H, d, J=2.20 Hz), 7.59 (1H, dd, J1=8.60 Hz, J2=2.20 Hz), 7.38 (1H, dd, J1=7.78 Hz, J2=1.65 Hz), 7.23 (1H, dd, J1=7.87 Hz, J2=1.28 Hz), 7.17 (1H, broad s), 7.13 (2H, td, J1=7.43 Hz, J2=1.28 Hz), 7.04 (1H, J=7.57 Hz, J2=1.71 Hz), 6.94 (1H, d, J=8.78 Hz), 5.40 (1H, s), 4.76 (1H, d, J=15.83 Hz), 4.68 (1H, d, J=15.83 Hz), 4.62 (2H, s), 4.04 (2H, m, J1=7.12 Hz), 3.77–3.63 (4H, m), 3.62 (3H, s), 2.94 (2H, t, J=8.32 Hz), 2.61 (2H, t, J=8.23 Hz), 2.35 (3H, s), 1.18 (3H, t, J=7.14)

Example 6

Methyl 4-(2-chlorophenyl)-6-[(2-{2-[4-(5-cyano-2-methyl-6-oxo(3-hydropyridyl))phenoxy]acetylamino}ethoxy)methyl]-5-(ethoxycarbonyl)-2-methyl-1,4-dihydropyridine-3-carboxylate (Compound 13) was synthesized according to Scheme V. The required 2-[4-(5-cyano-2-methyl-6-oxo-3-hydropyridyl)phenoxy]acetic acid was prepared according to Scheme VI, using the methods described in *J. Med. Chem.* 2002, 45, 1887–1900 and U.S. Pat. No. 5,051,431.

SCHEME VI

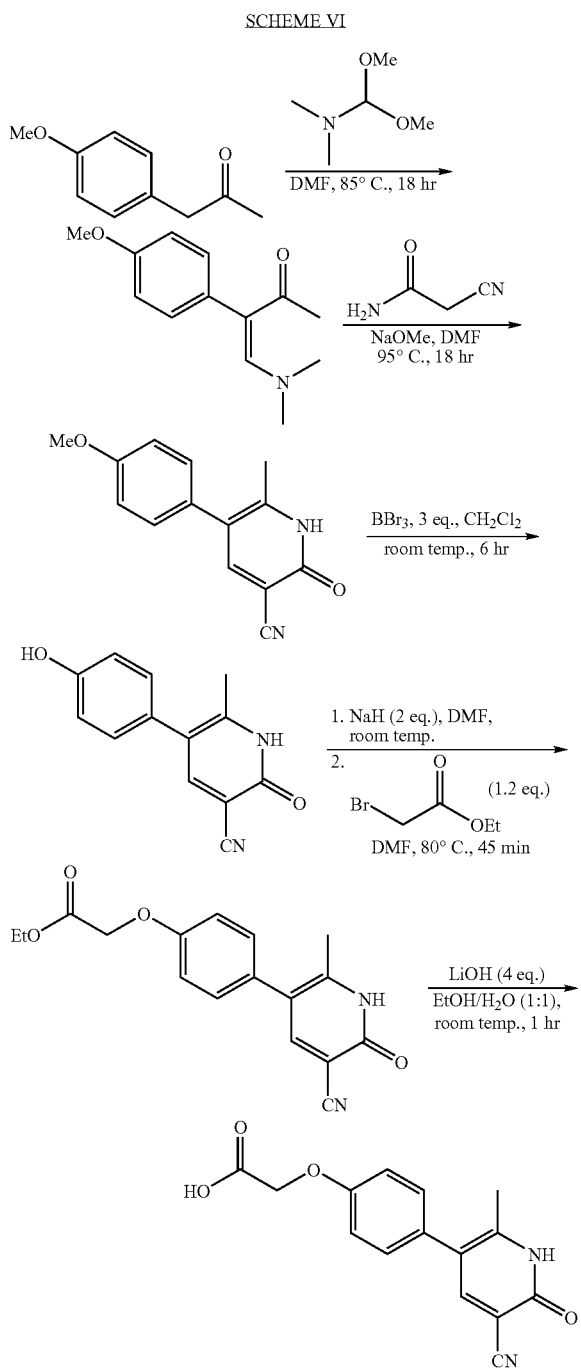

Synthesis of 4-Dimethylamino-3-(4-methoxy-phenyl)-but-3-en-2-one (3).

To a stirred solution of 1-(4-methoxy-phenyl)-propan-2-one (1, 8.37 g, 51.0 mmol) in N,N-dimethylformamide (200 mL) was added dimethoxymethyl-dimethyl-amine (2, 27 mL, 203 mmol). The reaction mixture was then stirred for 18 h at 85° C., allowed to cool to ambient temperature and excess solvent and reagents were removed under reduced pressure to give crude 4-dimethylamino-3-(4-methoxyphenyl)-but-3-en-2-one (3) as yellow oil which was used in the following step without further purification.

Synthesis of 5-(4-Methoxy-phenyl)-6-methyl-2-oxo-1,2-dihydropyridine-3-carbonitrile (5)

To a stirred solution of sodium hydride (60% dispersion in mineral oil, 4.5 g, 112 mmol) in N,N-dimethylformamide (100 mL) was added dropwise at 0° C. a solution of crude 4-dimethylamino-3-(4-methoxyphenyl)-but-3-en-2-one (3) from the previous step, 2-cyano-acetamide (4, 4.75 g, 56.5 mmol) and methanol (4.54 mL, 112 mmol) in N,N-dimethylformamide (50 mL). The reaction mixture was stirred at ambient temperature for 15 min and then at 95° C. for 18 h. After cooling to ambient temperature most of the solvent was removed under reduced pressure. The residue was hydrolysed with saturated aqueous ammonium chloride solution (100 mL). The precipitated solid was collected by filtration with suction, rinsed with water and diethyl ether and dried under vacuum to give 5-(4-methoxy-phenyl)-6-methyl-2-oxo-1,2-dihydro-pyridine-3-carbonitrile (5) as a brownish solid (10.0 g, 82% yield over two steps, 99% pure by LC-MS and $^1$H NMR), $^1$H NMR (400 MHz; CDCl$_3$): δ 7.70 (s, 1H); 7.19 (m, 2H); 6.72 (m, 2H); 3.73 (s, 3H); 1.71 (s, 3H).

Synthesis of 5-(4-Hydroxy-phenyl)-6-methyl-2-oxo-1,2-dihydropyridine-3-carbonitrile (6)

To a stirred solution of 5-(4-Methoxy-phenyl)-6-methyl-2-oxo-1,2-dihydro-pyridine-3-carbonitrile (5, 10.0 g, 41.6 mmol) in dichloromethane (200 mL) was added dropwise at 0° C. a solution of boron tribromide (11.8 mL, 125 mmol) in DCM (125 mL). The reaction mixture was stirred for 6 h at ambient temperature, poured into a mixture of ice and saturated ammonium chloride solution (100 mL) and stirred for 1 h at room temperature. The formed precipitate was filtered off, rinsed with water and re-dissolved in aqueous sodium hydroxide (2 N, 400 mL). The aqueous solution was washed with ethyl acetate (100 mL), acidified to pH 4 with aqueous hydrochloric acid (2 N) and extracted with ethyl acetate (3×200 mL). The combined organic phases were washed with brine (2×200 mL), dried (MgSO$_4$) and evaporated to dryness to give 5-(4-hydroxy-phenyl)-6-methyl-2-oxo-1,2-dihydro-pyridine-3-carbonitrile (6) as a yellow solid (3.25 g, 46% yield, 92% pure by LC-MS and $^1$H NMR), $^1$H NMR (400 MHz; CDCl$_3$): δ 7.70 (s, 1H); 7.13 (m, 2H); 6.68 (m, 2H); 1.71 (s, 3H).

Synthesis of [4-(5-Cyano-2-methyl-6-oxo-1,6-dihydro-pyridin-3-yl)phenoxy]-acetic acid ethyl ester (7)

To a stirred suspension of sodium hydride (60% dispersion in mineral oil, 1.16 g, 29.0 mmol) in N,N-dimethylformamide (50 mL), was added at 0° C. a solution of 5-(4-hydroxy-phenyl)-6-methyl-2-oxo-1,2-dihydro-pyridine-3-carbonitrile (6, 3.25 g, 14.4 mmol) in N,N-dimethylformamide (50 mL). The mixture was stirred at ambient temperature for 30 min. A solution of ethyl 2-bromoacetate (2.0 mL, 18.0 mmol) in N,N-dimethylformamide (10 mL) was added at 0° C., the mixture was stirred for 30 min at 0° C., for 30 min at ambient temperature and then for 45 min at 80° C. The mixture was allowed to cool to room temperature, concentrated in vacuo and re-dissolved in ethyl acetate (300 mL). The solution was extracted with water (3×150 mL). The combined aqueous layers were acidified to pH 2 with aqueous hydrochloric acid (1 N) and extracted with ethyl acetate (3×150 mL). The combined organic layers were dried (MgSO$_4$) and evaporated to dryness. The residue was purified by column chromatography on silica gel (50 g) using 2% methanol in dichloromethane as eluent to give [4-(5-Cyano-2-methyl-6-oxo-1,6-dihydro-pyridin-3-yl)phenoxy]-acetic acid ethyl ester (7) as light yellow powder (1.3 g, 29% yield, 80–90% pure by LC-MS and $^1$H NMR), $^1$H NMR (400 MHz; CDCl$_3$): δ 7.70 (d, 1H); 7.19 (m, 2H); 6.72 (m, 2H); 4.90 (s, 2H); 4.12 (q, 2H); 1.71 (s, 3H); 1.30 (t, 3H).

Synthesis of [4-(5-Cyano-2-methyl-6-oxo-1,6-dihydro-pyridin-3-yl)-phenoxy]-acetic acid (8)

To a stirred solution of [4-(5-Cyano-2-methyl-6-oxo-1,6-dihydro-pyridin-3-yl)phenoxy]-acetic acid ethyl ester (7, 1.3 g, 4.16 mmol) in a mixture of 1,4-dioxane (25 mL) and water (25 mL) was added lithium hydroxide mono hydrate (700 mg, 16.7 mmol). The reaction mixture was stirred for 2 h at ambient temperature, diluted with water (50 mL), washed with diethylether (2×25 mL), cooled to 0° C. and acidified to pH 2 with aqueous hydrochloric acid (5 N). After standing at ambient temperature overnight the formed precipitate was filtered off with suction, washed with water and dried under vacuum to give [4-(5-Cyano-2-methyl-6-oxo-1,6-dihydro-pyridin-3-yl)-phenoxy]-acetic acid (8) as light yellow crystalline solid (758 mg, 64% yield, 97% pure by LC-MS and $^1$H NMR), $^1$H NMR (400 MHz; CDCl$_3$): δ 7.70 (d, 1H); 7.20 (m, 2H); 6.73 (m, 2H); 4.88 (s, 2H); 1.71 (s, 3H).

L-type Ca+2 Channel Blocking Activity

Test compounds of the present invention are evaluated for their ability to inhibit calcium currents through voltage-sensitive calcium channels by any one of several methods known to those skilled in the art. Thus, affinity for L-type calcium channels may be determined by measuring the potency of the test compounds to displace standard reference ligands from calcium channels in membrane preparations. Alternatively, ability to block voltage-dependent calcium entry into cells may be evaluated by measuring $^{45}$Ca$^{+2}$ flux.

Example 7

Assay for Measuring Affinity of Compounds for L-type Calcium Channels

[$^3$H]nitrendipine, a selective blocker of L-type calcium channels, was used as a reference ligand for evaluating the ability of the test compounds to displace the reference ligand from rat cerebral cortex. Plasma membrane preparations from rat cerebral cortex were obtained as described by Schwartz et al. [*Br. J. Pharmacol.* 1985, 84, 511]. Protein concentrations were determined by the method of Lowry et al. [*J. Biol. Chem.* 1951, 193, 265]. 1 mL of plasma membrane preparation (1 mg of protein) was incubated with 0.11 nM [$^3$H]nitrendipine (80 Ci/mmol) and increasing concentrations of test compounds in 50 mM Tris-HCl buffer, pH 7.4 (total volume 2 mL). Incubation was carried out at 25° C. for 90 minutes; bound and free ligands were separated by rapid filtration through Whatman GF/B filters. The filters were rapidly washed with 20 mL of 50 mM Tris-HCl buffer, pH 7.4, and transferred to counting vials containing 10 mL of scintillation cocktail. Radioactivity was measured in a Packard counter and non-specific binding was measured in the presence of 10$^{-5}$ M nitendipine. The IC$_{50}$ (the concentration that inhibited the maximum specific binding of the ligand by 50%) of the test compounds was determined. The IC$_{50}$ values were converted into K$_i$ values using the Cheng-Prusoff equation. The results are presented in Table 1, below.

PDE-3 Inhibitory Activity

Example 8

Assay for Measuring cAMP PDE-3 Inhibitory Activity

Human platelet cyclic AMP phosphodiesterase was prepared according to the method of Alvarez et al. (*Mol. Pharmacol.* 1986, 29, 554). The PDE incubation medium contained 10 mM Tris-HCl buffer, pH 7.7, 10 mM MgSO$_4$, and 1 μM [$^3$H]AMP (0.2 μCi) in a total volume of 1.0 mL. Test compounds were dissolved in dimethyl sulfoxide (DMSO) immediately prior to addition to the incubation medium, and the resulting mixture was allowed to stand for 10 minutes prior to the addition of enzyme. Following the addition of PDE, the contents were mixed and incubated for 10 minutes at 30° C. Three assays each were performed for each of five test compound concentrations, the mean of the determinations (n=3) at each concentration was plotted, and IC$_{50}$ values were determined graphically. The results are presented in Table 1, below.

TABLE 1

| Compound | IC$_{50}$, Ca$^{+2}$ channel, nM | K$_i$, Ca$^{+2}$ channel, nM | IC$_{50}$, PDE-3, nM |
| --- | --- | --- | --- |
| Compound 5 | 205, 249 | 94.1, 125 | 300 |
| Compound 6 | 1250, 3500 | 574, 1700 | 270, 110 |
| Compound 7 | 313, 657 | 143, 320 | 340, 420 |
| Compound 8 | 630 | 280 | 80 nM |
| Compound 9 | 100 | 48 | 48 |
| Compound 10 | 4220 | 2250 | 270 |
| Compound 11 | 692 | 360 | 100 |
| Compound 12 | 479 | 212 | 240 |

Restoration of Calcium Homeostasis in Heart Tissue

Example 9

Assay for Measuring Contraction-relaxation in Guinea Pig Papillary Muscle

Male guinea pigs (400–500 g) were killed by cervical dislocation and the hearts were quickly removed, immersed in ice-cold, and oxygenated in Kreb's solution containing 113.1 mM NaCl, 4.6 mM KCl, 2.45 mM CaCl$_2$, 1.2 mM MgCl$_2$, 22.0 mM NaH$_2$PO$_4$, and 10.0 mM glucose; pH 7.4 with 95% O$_2$–5% CO$_2$. The ventricles were opened and papillary muscles were removed with chordae tandineae and a base of surrounding tissue intact. The tendinous ends of the muscles were ligated with silk thread, and the muscles were mounted in vertical, double-jacketed organ baths containing 10 mL of oxygenated Kreb's solution kept at 37° C. The tendinous end was attached to a Grass isometric force transducer, while a metal hook was inserted into the base of the muscle.

Following a 45-minute equilibration period under a 1 gram tension, control contractions were elicited by stimulating the muscle using stainless steel field electrodes at a frequency of 1.0 Hz, 2.0 ms duration. The amplitude of the stimulus was adjusted to be approximately 1.5 times the threshold amplitude sufficient to elicit a contraction of the tissues. Control contraction-relaxation cycles were recorded for 30 seconds continuously. Cumulative concentrations of Compound 5 or the PDE-3 inhibitor milrinone were then injected directly into the bath while the tissue was being stimulated. Contraction-relaxation recordings were made continuously, for 30 seconds per concentration. A series of washout contractions was recorded following a change of solution. When the amplitude of contraction returned to that measured in control conditions, a single concentration of positive control was then tested on the tissue in the same manner as Compound 5 and milrinone.

Contraction amplitude as well as the time courses of contraction and relaxation were quantified. All recordings were normalized against control values; statistical analysis of the results was made using t-tests or ANOVAs. As shown in FIG. 1, Compound 5 produced positive inotropic effect (increase in muscle contractility) in a dose-dependent manner. The maximum increase in contractility produced by Compound 5 was less than the maximum increase produced by milrinone.

Example 10

Paced Dog Model of Congestive Heart Failure

Compound 8 was evaluated in a paced dog model of congestive heart failure. Pacing-induced heart failure in the dog produces alterations in heart physiology and molecular signaling similar to what is seen in the failing human heart, making this an appropriate model to test compounds that can potentially improve calcium homeostasis and heart failure physiology. Heart failure was induced by increasing the heart rate to 220–240 beats per minute (bpm) for a six week period. The degree of heart failure was documented by both pressure measurements and echocardiogram (changes in contractility, ejection fraction, ventricular relaxation, fractional area shortening, isovolumic relaxation time). Compound 8 or the milrinone were administered following the induction of heart failure.

Systemic administration of Compound 8 demonstrated in vivo inhibition of PDE-3 and calcium channel antagonism. Dogs in heart failure that were treated with milrinone demonstrated ventricular tachycardia (a precursor of ventricular fibrillation and sudden cardiac death) which was present at all tested dosages. In contrast, no ventricular tachycardia was associated with administration of Compound 8. In addition, there was no apparent QT prolongation associated with administration of Compound 8 under acute conditions.

Figure 2:
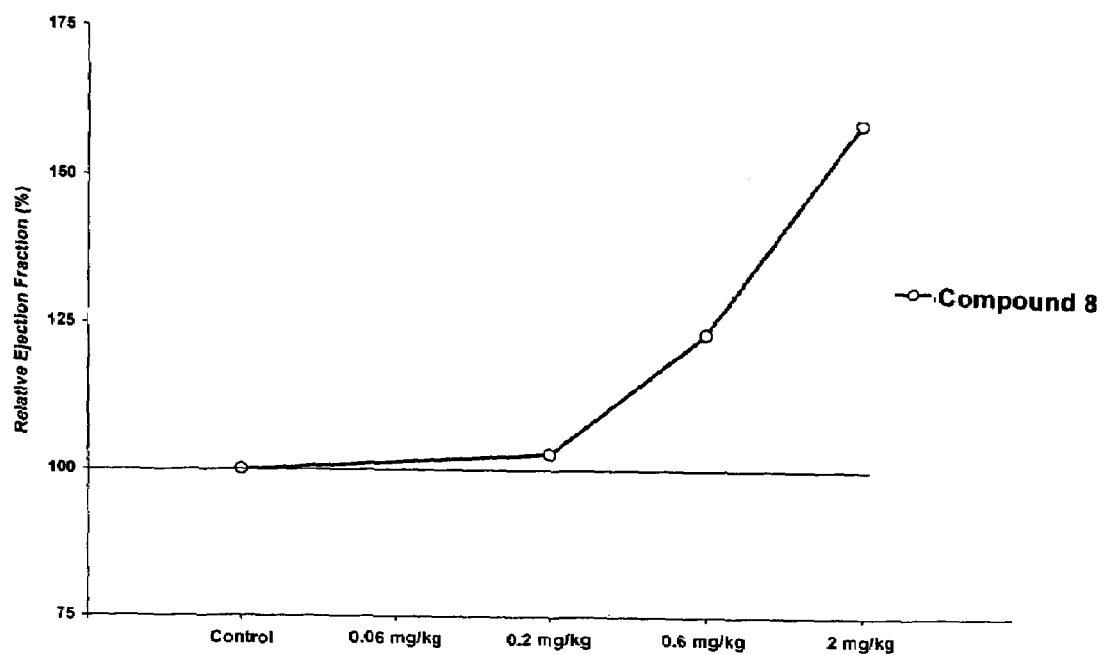
FIG. 2 is a graph showing improvement of cardiovascular function by Compound 8 in a dog model of congestive heart failure.
Figure 3:
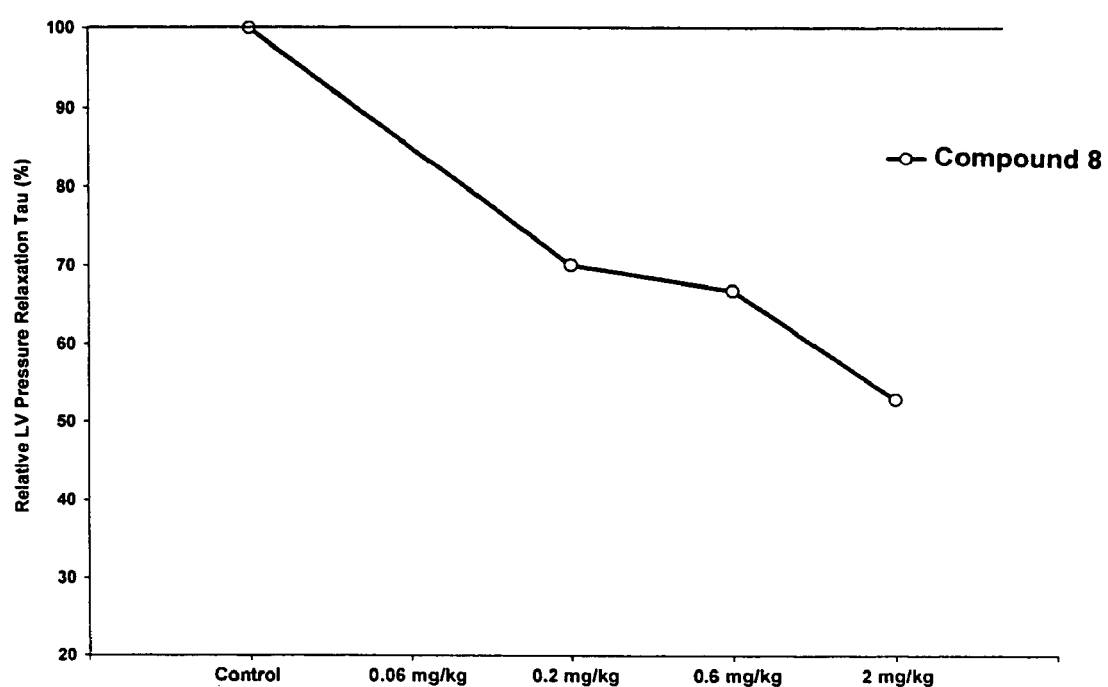
FIG. 3 is a graph showing enhancement of ventricular relaxation by Compound 8 in a dog model of congestive heart failure.

Compound 8 increased ventricular relaxation in a dose-dependent manner, (as measured by dp/dt min, Tau and isovolumic relaxation time) with a maximal increase of between 63–88% of that produced by milrinone. (see FIG. 3). Compound 8 also exhibited a dose-dependent response for contractility (dp/dt max) and ejection fraction with a maximal increase of between 53–61% of that produced by milrinone (see FIG. 2). These data show that simultaneous antagonism of the L-type calcium channel and PDE-3 by a compound of the present invention resulted in attenuation of calcium channel-dependent inotropic activity and maintenance of the ventricular relaxation produced by PDE inhibition alone. These data suggest that the inhibition of L-type calcium channel activity produced by Compound 8 antagonized the increase in calcium influx into the cardiac myocyte via the hyper-phosphorylated L-type calcium channel and thus prevented the toxicities associated with higher levels of PDE-3 inhibition (positive inotrophy, ventricular tachycardia and heart rate increases). These data are consistent with results obtained in the papillary muscle, isolated trabeculae, and cardiac myocytes in vitro.

All publications, patents and patent applications identified above are herein incorporated by reference.

The invention being thus described, it will be apparent to those skilled in the art that the same may be varied in many ways without departing from the spirit and scope of the invention. Such variations are included within the scope of the invention to be claimed.

We claim:
1. A compound of formula II

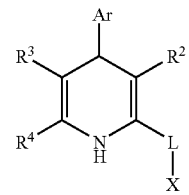

II or a pharmaceutically acceptable equivalent, an isomer or a mixture of isomers thereof, wherein:

$R^2$ and $R^3$ are independently —COOR$^7$, nitro, cyano or trifluoromethyl;

$R^7$ is $C_1$–$C_8$ alkyl, $C_2$–$C_8$ alkenyl or $C_2$–$C_8$ alkynyl, wherein the alkyl, alkenyl or alkynyl is optionally substituted with $C_1$–$C_4$ alkoxy or —NR$^5$R$^6$;

$R^4$ is hydrogen, halo, nitro, cyano, trifluoromethyl, amino, —NR$^5$R$^6$, $C_1$–$C_4$ alkoxy, $C_1$–$C_4$ alkylthio, $C_1$–$C_8$ alkyl, $C_2$–$C_8$ alkenyl or $C_2$–$C_8$ alkynyl, wherein one or more —CH$_2$— group(s) of the alkyl, alkenyl or alkynyl is/are optionally replaced with —O—, —S—, —SO$_2$— and/or —NR$^5$—, and the alkyl, alkenyl or alkynyl is optionally substituted with one or more oxo(s) and/or hydroxyl(s);

$R^5$ and $R^6$ are independently hydrogen, $C_1$–$C_8$ alkyl, $C_2$–$C_8$ alkenyl or $C_2$–$C_8$ alkynyl, wherein the alkyl, alkenyl or alkynyl is optionally substituted with phenyl or substituted phenyl;

L is a direct bond, $C_1$–$C_{12}$ alkylene, $C_2$–$C_{12}$ alkenylene or $C_2$–$C_{12}$ alkynylene, wherein one or more —CH$_2$— group(s) of the alkylene, alkenylene or alkynylene is/are optionally replaced with —O—, —S—, —SO$_2$— and/or —NR$^5$—, and the alkylene, alkenylene or alkynylene is optionally substituted with one or more oxo(s) and/or hydroxyl(s); and X is a moiety of formula J or Q

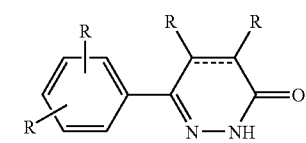

J

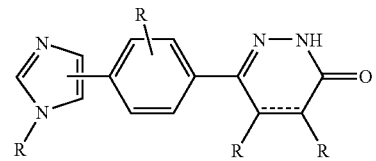

Q with X connected to L through any one R;

each R is independently a direct bond connecting X to L, hydrogen, halo, nitro, cyano, trifluoromethyl, amino, —NR$^5$R$^6$, $C_1$–$C_4$ alkoxy, $C_1$–$C_4$ alkylthio, —COOR$^7$, $C_1$–$C_{12}$ alkyl, $C_2$–$C_{12}$ alkenyl or $C_2$–$C_{12}$ alkynyl, wherein one or more —CH$_2$— group(s) of the alkyl, alkenyl or alkynyl is/are optionally replaced with —O—, —S—, —SO$_2$— and/or —NR$^5$—, and the alkyl, alkenyl or alkynyl is optionally substituted with one or more oxo(s) and/or hydroxyl(s), wherein only one R may be a direct bond connecting X to L; and Ar is an aryl that is optionally substituted in 1 to 3 position(s) with halo, nitro, cyano, trifluoromethyl, amino, —NR⁵R⁶, $C_1$–$C_4$ alkoxy, $C_1$–$C_4$ alkylthio, —COOR⁷, $C_1$–$C_8$ alkyl, $C_2$–$C_8$ alkenyl or $C_2$–$C_8$ alkynyl, wherein one or more —$CH_2$— group(s) of the alkyl, alkenyl or alkynyl is/are optionally replaced with —O—, —S—, —$SO_2$— and/or —NR⁵—, and the alkyl, alkenyl or alkynyl is optionally substituted with one or more oxo(s) and/or hydroxyl(s).

2. The compound of claim 1, wherein X is a moiety of formula J.

3. The compound of claim 2, wherein X is

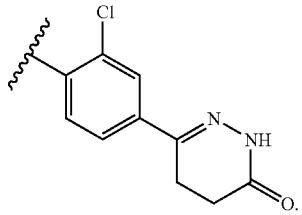

4. The compound of claim 1, wherein:
R² and R³ are independently -COOR⁷;
R⁷ is $C_1$–$C_3$ alkyl;
R⁴ is $C_1$–$C_4$ alkyl; and
Ar is a phenyl that is optionally substituted in 1 to 3 position(s) with halo or nitro.

5. The compound of claim 4, wherein:
R² is —COOCH₃ or —COOCH₂CH₃;
R³ is —COOCH₃;
R⁴ is methyl; and
Ar is 2-chlorophenyl.

6. The compound of claim 1, wherein:
L is —CH₂OCH₂CH₂NH(CO)CH₂CH₂CH₂O—, —CH₂OCH₂CH₂CH₂O—, or —CH₂OCH₂CH₂NH(CO)CH₂O—; and
X is a moiety of formula J.

7. The compound of claim 6, wherein:
L is —CH₂OCH₂CH₂NH(CO)CH₂O—; and
X is

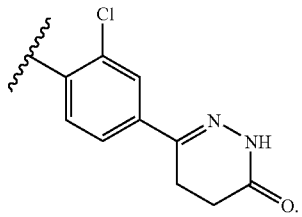

8. The compound of claim 7, wherein the compound is

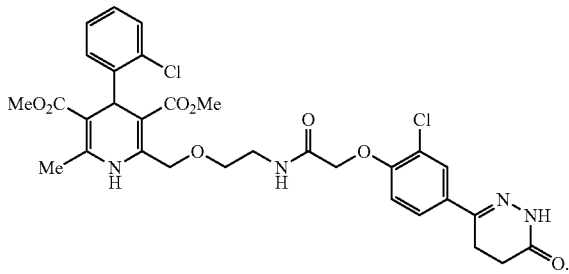

9. The compound of claim 8, which is a non-racemic mixture wherein the R configuration is enriched.

10. The compound of claim 8, which is a non-racemic mixture wherein the S configuration is enriched.

11. The compound of claim 1, wherein X is a moiety of formula Q.

12. The compound of claim 4, wherein:
L is —CH₂OCH₂CH₂NH(CO)CH₂CH₂CH₂O—, —CH₂OCH₂CH₂CH₂O—, or —CH₂OCH₂CH₂NH(CO)CH₂O—; and
X is a moiety of formula Q.

13. A compound having the formula

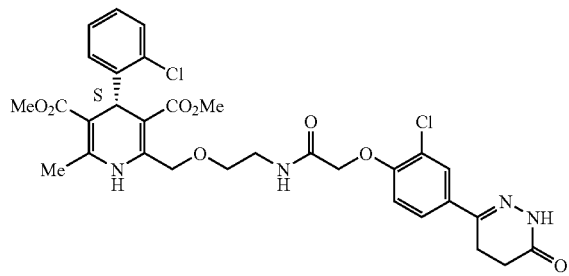

or a pharmaceutically acceptable salt or hydrate thereof.

14. A pharmaceutical composition comprising: p1 (i) an effective amount of a compound of any one of claims 1, 2–10, and 11–13; and
(ii) a pharmaceutically acceptable carrier.

* * * * *